US012186439B2

(12) United States Patent
Trapani

(10) Patent No.: US 12,186,439 B2
(45) Date of Patent: Jan. 7, 2025

(54) METHOD AND STERILIZATION SYSTEM FOR IMPROVING DUTY CYCLE OF ROBOTIC SYSTEM AND ULTRAVIOLET (UV) EMITTERS DISINFECTING CLOSED ENVIRONMENT

(71) Applicant: STERILIZ, LLC, Rochester, NY (US)

(72) Inventor: Samuel Richard Trapani, Rochester, NY (US)

(73) Assignee: STERILIZ, LLC, Rochester, NY (US)

( * ) Notice: Subject to any disclaimer, the term of this patent is extended or adjusted under 35 U.S.C. 154(b) by 924 days.

(21) Appl. No.: 17/244,433

(22) Filed: Apr. 29, 2021

(65) Prior Publication Data

US 2021/0244839 A1    Aug. 12, 2021

Related U.S. Application Data

(60) Continuation-in-part of application No. 16/164,150, filed on Oct. 18, 2018, now Pat. No. 11,154,629.
(Continued)

(51) Int. Cl.
*A61L 2/10* (2006.01)
*A61L 2/20* (2006.01)
(Continued)

(52) U.S. Cl.
CPC ............... *A61L 2/10* (2013.01); *A61L 2/202* (2013.01); *A61L 2/208* (2013.01); *A61L 2/24* (2013.01);
(Continued)

(58) Field of Classification Search
CPC ........................................................ A61L 2/10
See application file for complete search history.

(56) References Cited

U.S. PATENT DOCUMENTS 3,861,875 A    1/1975 Joslyn
5,114,670 A    5/1992 Duffey
(Continued)

OTHER PUBLICATIONS

"Enhanced Environmental Disinfection Systems", Enhanced Environmental Disinfection Systems, Health Devices, May 2011. pp 150-162, ECRI Institute, www.ecri.org., May 2011, 150-162.
(Continued)

*Primary Examiner* — Donald R Spamer
(74) *Attorney, Agent, or Firm* — HULSEY P.C.

(57) ABSTRACT

Method, sterilization system and robotic system for improving duty cycle of Ultraviolet (UV) emitter modules disinfecting closed environment. Sterilization system includes robotic system and plurality of UV emitter modules. Robotic system receives signal corresponding to discharge of battery from one of plurality of UV emitter modules. Each of plurality of UV emitter modules includes UV light source for disinfecting closed environment. Robotic system detects location of UV emitter module amongst plurality of UV emitter modules and maneuvers to location of UV emitter module, mounts UV emitter module and maneuvers UV emitter module to charging dock for charging battery of UV emitter module. After charging, robotic system maneuvers UV emitter module to pre-defined area for disinfecting pre-defined area of closed environment. Robotic system includes battery charged through UV emitter module when UV emitter module is getting charged, or when UV emitter module mounted to robotic system includes battery that is fully charged.

20 Claims, 15 Drawing Sheets

Related U.S. Application Data which is a continuation-in-part of application No. 15/169,164, filed on May 31, 2016, now Pat. No. 10,226,541, which is a continuation of application No. 14/263,774, filed on Apr. 28, 2014, now Pat. No. 10,010,633, and a division of application No. 13/964,874, filed on Aug. 12, 2013, now Pat. No. 9,345,798, said application No. 14/263,774 is a continuation-in-part of application No. 13/964,874, filed on Aug. 12, 2013, now Pat. No. 9,345,798, which is a continuation-in-part of application No. 13/446,563, filed on Apr. 13, 2012, now abandoned.

(60) Provisional application No. 63/029,292, filed on May 22, 2020, provisional application No. 61/475,722, filed on Apr. 15, 2011.

(51) Int. Cl.
*A61L 2/24* (2006.01)
*A61L 9/015* (2006.01)
*A61L 9/20* (2006.01)
*G01J 1/02* (2006.01)
*G01J 1/42* (2006.01)

(52) U.S. Cl.
CPC ............ *A61L 9/015* (2013.01); *A61L 9/20* (2013.01); *A61L 2202/11* (2013.01); *A61L 2202/14* (2013.01); *A61L 2202/16* (2013.01); *A61L 2202/25* (2013.01); *G01J 2001/0276* (2013.01); *G01J 1/429* (2013.01)

(56) References Cited

U.S. PATENT DOCUMENTS

| | | | |
|---|---|---|---|
| 5,650,800 | A | 7/1997 | Benson |
| 6,592,816 | B1 | 7/2003 | Ebel et al. |
| 6,656,424 | B1 | 12/2003 | Deal |
| 6,662,099 | B2 | 12/2003 | Knaian et al. |
| 6,911,177 | B2 | 6/2005 | Deal |
| 7,638,970 | B1 | 12/2009 | Gebhard |
| 8,067,750 | B2 | 11/2011 | Deal |
| 2005/0168154 | A1 | 8/2005 | Erickson et al. |
| 2005/0242290 | A1 | 11/2005 | May et al. |
| 2006/0120915 | A1 | 6/2006 | Lewandowski |
| 2007/0008117 | A1 | 1/2007 | Parker et al. |
| 2007/0023710 | A1 | 2/2007 | Tom |
| 2007/0048176 | A1 | 3/2007 | Orrico |
| 2007/0050191 | A1 | 3/2007 | Weider et al. |
| 2007/0099643 | A1 | 5/2007 | Almeda et al. |
| 2007/0102025 | A1 | 5/2007 | Ahn et al. |
| 2010/0061887 | A1 | 3/2010 | Harper |
| 2011/0168898 | A1 | 7/2011 | Statham et al. |
| 2012/0223216 | A1* | 9/2012 | Flaherty ............... G05D 1/0242 901/1 |
| 2012/0305787 | A1 | 12/2012 | Henson |
| 2015/0209460 | A1* | 7/2015 | Kreitenberg ............ A61L 2/10 422/24 |
| 2021/0299868 | A1* | 9/2021 | Vitzrabin ................. A61L 2/24 |
| 2021/0402446 | A1* | 12/2021 | Thompson ........... G05D 1/0251 |
| 2022/0001061 | A1* | 1/2022 | Hoang ...................... A61L 2/24 |
| 2022/0088241 | A1* | 3/2022 | Braverman ............... A61L 9/20 |

OTHER PUBLICATIONS

"UV Power Meter", Hamamatsu. "UV Power Meter". taken from screen capture by the Internet Archive Wayback Machine on Jan. 2, 2010.

Boyce, John M. et al., "Terminal Decontamination of Patient Rooms Using an Automated Mobile UV Light Unit", Boyce, John M. et al., Terminal Decontamination of Patient Rooms Using an Automated Mobile UV Light Unit, Infection Control and Hospital Epidemiology, Aug. 2011. pp. 737-742, vol. 32, No. 8, The Society for Healthcare Epidemiology of America, USA., Aug. 2011, 737-742.

Rutala, William A. et al., "Are Room Decontamination Units Needed to Prevent Transmission of Environmental Pathogens?", Rutala, William A. et al., Are Room Decontamination Units Needed to Prevent Transmission of Environmental Pathogens?, Infection Control and Hospital Epidemiology, Aug. 2011. pp. 743-747, vol. 32, No. 8, The Society for Healthcare Epidemiology of America, Aug. 2011, 737-742.

Mao et al. Sampling Frequency Optimization in Wireless Sensor Network-Based Control System. Shanghai Jiao Tong University. APWeb Workshops. 2006.

* cited by examiner

METHOD AND STERILIZATION SYSTEM FOR IMPROVING DUTY CYCLE OF ROBOTIC SYSTEM AND ULTRAVIOLET (UV) EMITTERS DISINFECTING CLOSED ENVIRONMENT

CROSS-REFERENCE TO RELATED APPLICATIONS

This application claims priority to a U.S. Provisional Patent Application No. 63/029,292, filed May 22, 2020; which is a continuation-in-part of U.S. application Ser. No. 16/164,150, filed Oct. 18, 2018; which is a continuation-in-part of U.S. application Ser. No. 15/169,164, filed May 31, 2016 (now U.S. Pat. No. 10,226,541); which is a continuation of U.S. application Ser. No. 14/263,774, filed Apr. 28, 2014 (now U.S. Pat. No. 10,010,633); which is a continuation-in-part of U.S. application Ser. No. 13/964,874, filed Aug. 12, 2013 (now U.S. Pat. No. 9,345,798); which is a CIP of Ser. No. 13/446,563, filed Apr. 13, 2012 (now abandoned); which claims priority to U.S. Provisional Patent Application No. 61/475,722, filed Apr. 15, 2011; and U.S. application Ser. No. 15/169,164 is a divisional of U.S. application Ser. No. 13/964,874, filed Aug. 12, 2013 (now U.S. Pat. No. 9,345,798); all of which are hereby incorporated by reference in their entirety.

FIELD OF THE INVENTION

The present invention relates to disinfection. More specifically, the present invention relates to disinfection of pathogens using ultraviolet (UV) emitter modules, while also improving duty cycle of UV emitter modules and robotic system that is configured to maneuver UV emitter modules.

BACKGROUND OF THE INVENTION

In the U.S. each year, more people die from hospital infections than from AIDS, breast cancer, and auto accidents combined. These infections are the fourth leading cause of death, with current annual estimates of 2,000,000 infections, 100,000 deaths, and added costs of $45 billion. Somewhere between 5-10% of all patients admitted to a hospital acquire an infection while in that hospital. Even with such extreme statistics, many industry experts consider the problem to be severely underestimated.

Currently, *Clostridium difficile* (*C. diff*) is one of the most problematic pathogens in the healthcare industry. It causes *C. diff* Infection (CDI) that sickens and kills humans. The Centers for Disease Control (CDC) states that *C. diff* spores are transferred to patients mainly via the hands of healthcare personnel who have touched a contaminated surface or item. They also say that to reduce the chance of spreading pathogens and subsequent disease, surfaces must be cleaned better.

Current cleaning methods such as a chemical disinfection are not working as a stand-alone practice. Additional measures need to be taken to reduce patient and healthcare professionals' risks. UV light is known to destroy pathogens in water supplies and HVAC systems. In recent years, products also have been developed that utilize UV to disinfect surfaces and air.

It is well-known that the UV portion of the light spectrum has the ability to inactivate the DNA of pathogens, making them unable to multiply. Medical uses of UV light include sterilization of surfaces and air without the use of chemicals. Well documented studies identify the specific amount (dosage) of UV light necessary to disinfect and sterilize surfaces and air.

One type of existing UV disinfection equipment uses either a manually operated switch or a timer to deliver UV light for a period of time. Another type of existing UV disinfection equipment is a system that measures reflected UV light, generally at the emitter, to control how much time the UV light is delivered. Both of these types of equipment are unable to definitively deliver a specific dosage to a surface or volume of air because no measurement is taken at the location of interest. This problem results in surfaces and air being over- or under-treated. In the case of over-treating, excess treatment time slows down the facility's operations, thus adding to operating costs and reducing throughput, and results in excess exposure to room surfaces, which causes faster breakdown of the materials from which the surfaces are made. In the case of under-treating, disinfection or sterilization is not assured, resulting in reduced efficacy and increased exposure to liability lawsuits.

In addition, UV disinfection equipment is placed over a base. Subsequently, the base is maneuvered either manually or automatically to a desired area to sterilize or disinfect desired area. Generally, a user has to be present at all times to maneuver the UV disinfection equipment to the desired area for operating the UV disinfection equipment. Alternatively, UV disinfection equipment mounts to a motorized base or robotic system permanently or semi-permanently. The motorized base or robotic system includes power source such as a battery for maneuvering the robotic UV disinfection equipment. Since it takes significant time to recharge the battery, the robotic UV disinfection equipment cannot be used for disinfecting desired area when it is being charged thus resulting in reduced duty cycle for the robotic UV disinfection equipment.

SUMMARY OF THE INVENTION

The present invention provides room disinfection and/or sterilization methods and apparatuses that satisfy the demands discussed above while improving on known shortcomings in the conventional art.

The present invention includes a mobile system which, when used properly, automatically delivers UV-C light to all surfaces within a treatment space, including hard-to-clean, high-touch surfaces such as keyboards, computers, and bed rails, yielding a significantly cleaner, safer environment.

When compared to other systems and techniques, the present invention provides faster processing-time and critical data capture that clearly demonstrates treated areas have received the necessary dosage of UV-C light needed to eradicate dangerous pathogens effectively. Another benefit of UV-C disinfection is that it leaves no harmful residue or vapors. The room is immediately available for occupancy.

The present invention includes a room disinfection and sterilization system utilizing UV light to cause permanent and fatal injury to the pathogens that cause illness and death to humans. This system includes an emitter that produces UV light, one or more remote wired or wireless UV light sensors that measure the intensity of UV light incident upon them, one or more remote wired or wireless door sensor safety stop switches which cause the system to stop emitting UV light in the event the door being monitored is opened or if the safety stop switch is depressed, a wired or wireless remote control to operate the system, and a central computer with wireless local area network (WLAN, e.g., Wi-Fi, WICAD, Bluetooth, 802.11, 802.15, 3G, 4G, CDMA, or other suitable technology) connect-ability to access the internet and provide local and remote logging of disinfection cycles or jobs. In some embodiments, the device of the present disclosure may include its own Wi-Fi access point, along with an Internet bridge (for example, a cellular modem). In some embodiments, the remote control may be a standard iPod or other PDA/smartphone/tablet/handheld device.

The present invention delivers lethal UVC light doses into all areas of complex environments, destroying viruses, spores, and drug-resistant bacteria, even in a room's shadowed areas. Its unique, next-generation remote sensors make this the only system that can measure how much UVC energy reaches every corner of a treatment space.

The present invention employs at least one remote sensor which definitively measures the precise dosage of UV light delivered to the location of interest. Data recording and reporting are necessary for tracking and analyzing infections acquired in facilities where disinfection occurs. A significant difference between the present invention and conventional equipment and systems is the ability to store, retrieve, report and analyze such data. The present invention employs local storage of such data on the hard disk drive of its computer controller and remote data storage via up-linking to a remote internet host server for others to access.

Studies have shown that a significant problem with UVC disinfection of surfaces occurs when the subject surface is not exposed to direct UVC light. Instead, the subject surface may be exposed to UVC light that is reflected off other surfaces. The intensity of this reflected light is often much lower than that of direct UVC light resulting in lower inactivation of pathogens. One possible solution to help improve inactivation of pathogens is to reposition the UVC emitter throughout the disinfection treatment of the space being treated. Another possible solution is to use multiple UVC emitters. In one preferred embodiment of the present invention, a multiple emitter configuration is used to disinfect the space. An issue with using multiple emitters is the distance between the control station and the emitters. The usable distance for the control station to communicate, in an indoor environment such as a hospital, with an emitter, is limited to approximately 30 feet. The present invention solves the distance limitation by establishing data communication between the control station and only one emitter, which is a Master emitter, and which remains located within the limited distance. The other emitters located within the space to be disinfected are Slave emitters, which communicate with the Master emitter rather than the control station. Another issue with multiple emitters within a given space is a limited amount of AC power available in the space. Atypical UVC emitter draws 15 amps. If more than one emitter is plugged into the same AC outlet, and are energized at the same time, the resulting electrical overload may trip a circuit breaker. resulting in a loss of power to two emitters during the disinfection process. The present invention solves this problem by monitoring either voltage drop or current draw, and shutting off the emitter or emitters using too much power.

In addition, the present invention provides a sterilization system including separate Ultraviolet (UV) emitter modules and robotic system, each having their own resources such that robotic system may return UV emitter module with discharged battery to a charging dock and leave it there to charge and pick up another UV emitter module with fully charged battery to disinfect the closed environment.

The sterilization system includes robotic system and plurality of Ultraviolet (UV) emitter modules. Robotic system receives signal corresponding to discharge of battery from one of plurality of UV emitter modules. Each of plurality of UV emitter modules includes Ultraviolet (UV) light source for disinfecting closed environment. Robotic system detects location of UV emitter module amongst plurality of UV emitter modules and maneuvers to location of UV emitter module.

After reaching the location of UV emitter module, robotic system mounts UV emitter module and maneuvers UV emitter module to charging dock for charging battery of UV emitter module. After charging, robotic system maneuvers UV emitter module to a pre-defined area for disinfecting pre-defined area of closed environment. In other words, robotic system maneuvers UV emitter module with discharged battery to charging dock and leaves it there to charge. After charging the battery, robotic system picks up the UV emitter module with fully charged battery to disinfect the closed environment.

In one embodiment, robotic system includes emitter interface for connecting robotic system to UV emitter module. Emitter interface allows charging the battery of robotic system when charging dock charges the battery of UV emitter module. Alternatively, emitter interface allows charging battery of robotic system through the UV emitter module when UV emitter module includes a battery that is fully charged.

In one advantageous feature of present invention, battery of robotic system may be continuously get charged or recharged from connected UV emitter modules, thereby allowing robotic system and UV emitter modules to have a 100% duty cycle. This ensures uninterrupted operation of robotic system and UV emitter modules for disinfecting closed environment using UV emitter modules. Further, this saves cost and manhours for users.

These and other advantages of the present invention will be apparent from the description provided herein. Additional systems, methods, features and advantages of the present invention will become apparent to one with ordinary skill in the art upon examination of the following drawings and detailed description of the preferred embodiments.

BRIEF DESCRIPTIONS OF THE DRAWINGS

The features, nature, and advantages of the present invention will become more apparent from the detailed description set forth below in conjunction with the drawings, wherein.

DETAILED DESCRIPTION OF THE PREFERRED EMBODIMENTS

Figure 1:
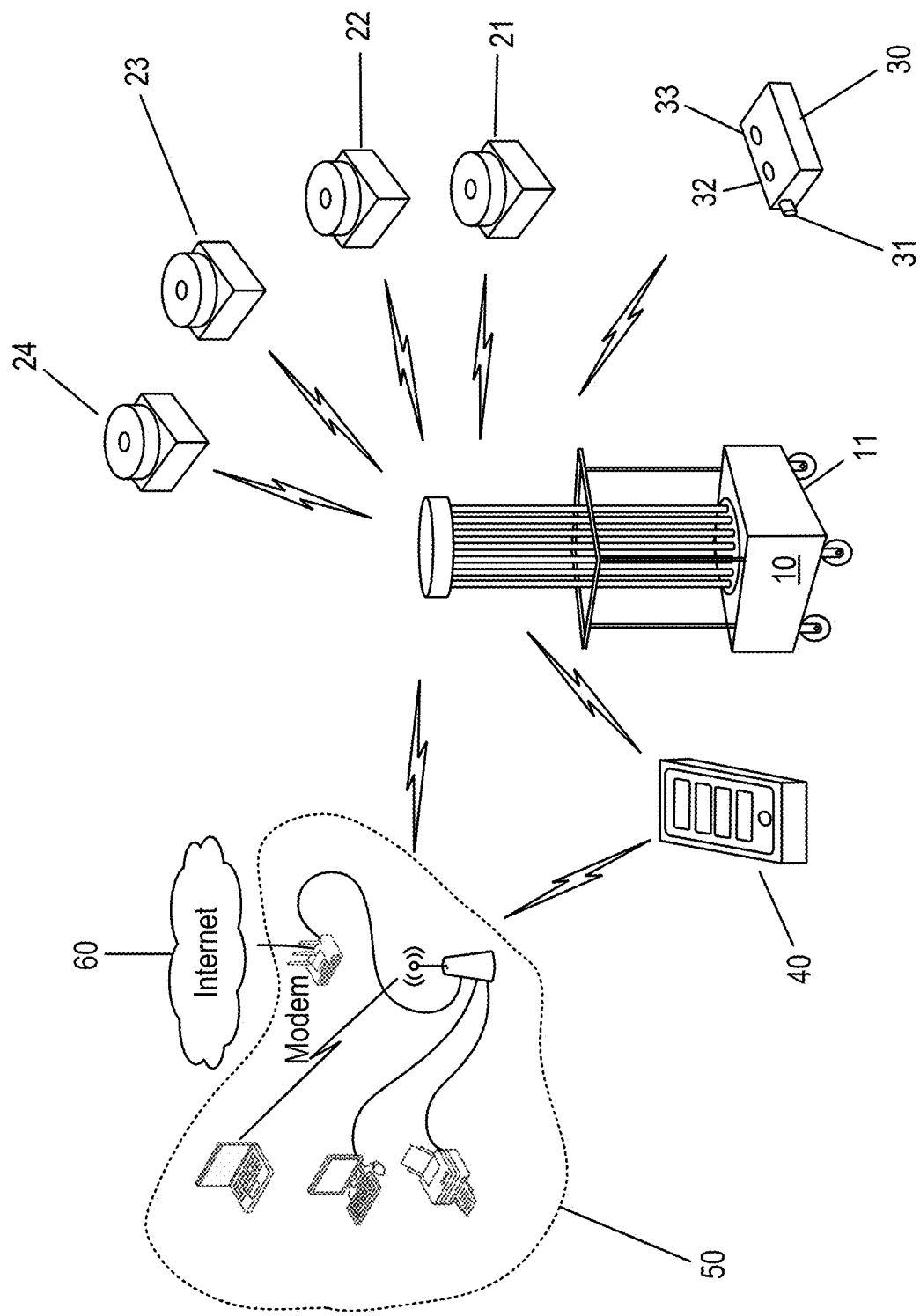
FIG. 1 is a perspective view of a disinfection system, in accordance with the present invention.

The present invention will be understood more readily by reference to the following detailed description of the presently preferred embodiments.

Reference will now be made in detail to certain presently preferred embodiments of the invention, examples of which are illustrated in the accompanying drawings. Wherever possible, the same reference numerals are used throughout the drawings to refer to the same or like parts.

As broadly embodied in FIG. 1, a sterilization system includes an emitter 10, a sensing system consisting of UV sensors 21-24, door sensor 30, a remote control 40, an optional wireless local area network (WLAN) 50, and an optional Internet connection 60 for the optional WLAN.

In more detail with reference to FIG. 1, the emitter subsystem includes the emitter 10 which is a mobile structure on wheels with a plurality of lamps that emit ultraviolet light when energized by their corresponding electronic ballast(s). Other possible embodiments of an emitter may be a mobile structure with another means for transporting without the use of integrated wheels, or a stationary structure. This subsystem further includes a central computer 11, which executes a software program that controls energization of the UV lamps and ballasts through the cycling of an interconnected relay. Computer 11 communicates with the sensing subsystem's remote UV sensors 21-24, which provide UV light level readings used by computer 11 to determine when a previously programmed dose of incident UV light has been delivered to each of the remote sensor locations.

The dosage setting is determined by the specific pathogen(s) the operator wants to eradicate. For example, to deliver a disinfection dosage of UV light for the elimination of *Escherichia coli* (*E. coli*) requires 6,600 microwatt-seconds/centimeter-squared for a 100:1 reduction (2 log) in *E. coli*; thus, the setting would be 6,600. Existing systems and equipment do not utilize remote sensor(s) for surface and air disinfection therefore they do not offer a way to definitively deliver this dosage to a remote location. The appropriate dosages to provide a particular log reduction in a particular pathogen are well known in the art. The present invention is not limited to any particular pathogen, disinfection level, or UV dosage.

Because UV light is harmful to humans, computer 11 communicates with door sensor 30, and if the monitored door has been opened during a disinfection cycle, which may indicate a person has entered the room being treated, the lamps are immediately turned off to prevent injury. The human-computer interface (HCI) may be accomplished via remote control 40, which is used to configure the type and number of sensors to be used for a particular job; to select the minimum dosage of UV light to deliver to each UV sensor; to begin, pause and end a job; and to view job reports stored on computer 11. Pausing the job may be advantageous for various reasons, including the possibility of re-positioning the emitter mid-job in order to obtain fuller coverage of the room. Computer 11 communicates with a remote web server, via the optional internet connected WLAN 50 (if present), to post job reports and status for remote access by password-protected users. The emitter subsystem contains a battery that keeps the computer energized when the subsystem is not plugged into the facility's electric utility. This battery is automatically recharged as needed from the facility's electric when the subsystem is plugged in. The emitter subsystem also has docks for recharging system sensors that operate by battery power.

Optional components of the present invention may be included in order to increase efficacy against particular pathogens. For example, in addition to using UV light, the device may further use a humidity generating device, an ozone generating device, and/or a vaporized hydrogen peroxide gas generating device. The combination of these optional components may provide better and faster disinfection than UV alone.

An integral part of the sterilization system is the sensing subsystem of FIG. 1. The UV light sensing system will measure actual incident light at least one particular site(s) in an area. An advantage of using incident light over reflected light is that with incident light, sensors can be placed at any site to guarantee that UV radiation reaches a certain minimum dosage at that site. UV sensors 21-24 are designed to measure the total UV light incident upon them. Once all active sensors have received the desired dose, the disinfection procedure is considered complete. One method of measuring total incident UV light is to employ a cosine-corrected sensor, which accounts for all light incident upon it from a full 180-degree solid angle. Another method utilizes multiple sensors, incorporated into a single sensor array, to measure the UV light from various angles of incidence and then to utilize an algorithm to integrate the total light incident upon the sensors to obtain the total incident light from a full 180-degree solid angle. Other known methods exist to measure the total incident UV light upon a sensor, and they are not precluded. For example, the sensors may make one or more instantaneous light measurements (perhaps after waiting for an initial warm-up period), and then calculate total dosage by assuming that the light level remains constant. Unless all the energy is integrated accurately, regardless of the method, it is difficult to determine the actual dosage of UV light delivered. Further, by measuring incident light, the system will not over-radiate an area. This allows for the shortest time for disinfection treatment before re-deployment into another area.

Over-radiating is disadvantageous in the fact that that the rays could cause damage to surfaces in the area unnecessarily. This is in addition to the fact that fewer areas can be finished per unit time. When operating, the UV sensor(s) are designed and programmed to continually measure incident UV light. The intensity measured is converted into a voltage, which is sampled by an analog to digital (A/D) converter, which is part of the UV sensor sub-system. The digital data may then be communicated to central computer 11. In addition to the intensity, a remote sensor may communicate a value representing the charge state of its internal battery. In this way, central computer 11 can be informed ahead of time how much battery life may be left in each remote sensor. The preferred embodiment of this communication system is a wireless system, but a wired communication system also is within the scope of the invention. Wireless operation can be accomplished from any number of remote UV sensors back to central computer 11 using one of any number of wireless protocols. A preferred implementation uses four UV sensors 21-24, but any number of UV sensors is within the scope of the invention. A preferred wireless protocol is the 802.15.4 Zigbee standard. In addition to wireless UV sensors 21-24, wireless door sensor 30 is included in the network of FIG. 1.

Wireless UV sensors 21-24 preferably are rechargeable battery-operated units although non-rechargeable or AC-powered units are not precluded. While in operation, the unit may operate completely on battery power. When not in operation, the sensor can be stored in its cradle on the emitter unit, or some other location, at which time re-charging occurs. The set of sensors are operated such that they transmit with different time periods allowing for a lower probability that two units will transmit at the same time. Another preferred embodiment uses buffering of the data at central computer 11 so that if multiple transmissions by sensors occur, the receiver at central computer 11 will not miss any one of them. In yet another preferred embodiment, a central computer 11 initiates the request for data from the door and the UV sensors on a one-by-one basis thereby eliminating the potential for two units to transmit at the same time. The UV sensors 21-24 are expected to see a relatively constant incident light intensity, and as such, time between transmissions, or the transmission period, can be relatively long. An example transmission period is 10 seconds, but this could range from as short as a few milliseconds to as long as several hours and is easily changed by the operator via the system software.

In the case of a nominal 10 second transmission period, the individual sensors can in one embodiment be programmed to retransmit at a time period equal to a prime number of milliseconds close to 10 seconds or 10,000 milliseconds. For example, sensor 1 might transmit at 9949 milliseconds, sensor 2 at 9967 milliseconds, sensor 3 at 9973 milliseconds and sensor 4 at 10007 milliseconds. These are all prime numbers of milliseconds close to 10 seconds. Setting the transmission period to these time periods greatly reduces the probability of two or more transmissions occurring at the same time. This does not preclude the use of similar time periods amongst UV sensors 21-24 as well.

Central computer 11 may receive the UV sensors' transmissions at the programmed transmission times and then calculate the time difference between receptions of information from each individual sensor in order to integrate the total incident light energy from each sensor and ensure that at least the prescribed dosage has been delivered to each particular sensor location.

This scheme provides another safeguard, because central computer 11 can detect if no messages are being received from a particular sensor for some maximum time from the time the last transmission was received. This condition could occur because of a completely discharged battery or a defect in the sensing unit, in which case operator interaction would be required.

Each system may be equipped with door sensor 30 (or in some embodiments multiple door sensors) for emergency shutoff purposes. Door sensor 30 includes door detector 31. If the door opens or closes, central computer 11 will receive a notification from door detector 31. If this event occurs while emitter 10 is operating and emitting UV light, then central computer 11 will shut down emitter 10. In addition to door detector 31, door sensor 30 also includes emergency shutoff detector 32, which could be used by an operator to shut down the system even if the door is closed. All of these events are distinguishable by central computer 11 by the message sent to it from door sensor 30. Central computer 11 knows which of the above-mentioned events occurred because of the digital information transmitted to it.

Latching may be provided on emergency shutoff detector 32. Once emergency shutoff detector 32 is actuated, the indication will remain until reset. The current reset condition occurs when the door is open; however, other methods to reset are possible. Door sensor 30 may also communicate its battery state back to central computer 11 so that the system will know when the battery needs to be recharged, and the operator will be so notified.

Once the remote sensor(s) and UV emitter are placed where desired, the operator exits the room and begins the activation sequence by placing door sensor 30 in position at the door such that the sensor can detect if the door is opened or closed, or if there is a change from open to closed or vice-versa.

Next, the operator must actuate arming detector 33 located on the door sensor 30. A designed safety feature prevents the system from being armed unless door sensor 30 indicates the door is closed. An open door or a door that is closed when armed and then opened will reset the system to the unarmed state. This design requires the operator to make sure that the door is closed before re-arming emitter 10.

This is of course only one embodiment of a method to arm the system. Another wired or wireless arming detector placed directly on the emitter could also provide a similar function. Under this condition, the door must be open to arm the system. If the door is open, the operator can actuate the arming detector 33 on the emitter 10. After this detector 33 is actuated and latched (programmed to keep its state as "armed"), the door must close. Once the door is closed, remote control 40 could start the system. If the door has not closed, remote control 40 will not be able to start emitter 10. If the door opened after the emitter 10 started, the emitter 10 would shut down and cease emitting UV light.

Emitter 10 may include one or more additional "drone" emitters. These are additional lights that may be added to the space in order to increase coverage and/or brightness and thereby decrease cleaning time. The drone emitter(s) may be controlled by central computer 11 either by wired or wireless communications.

Door sensor 30 may encode the different switch conditions into a unique voltage measurement. This voltage may be converted to a digital value by an A/D converter, which may be part of door sensor 30 and then sent to central computer 11. The existence of the 3 detectors creates a maximum of 8 different voltage settings. In one embodiment with arming detector 33 as part of door sensor 30, when the door is open, the state of the arming detector 33 is in a "don't care" condition (X). As such, only 6 states need be detected. An example encoding of the door switch Door Arming Emergency Voltage A/D (hex Position Switch Shutoff Switch Operation (V) code) is a Closed Armed Open Normal 1 AAA Closed Unarmed Open Waiting 0.82 8BF for Arm Closed Armed Closed Shutdown 1.39 ED3 Closed Unarmed Closed Shutdown 1.21 CE8 Open X Open Shutdown 0 000 Open X Closed Shutdown 0.39 428.

Because door sensor 30 communicates such critical information, its time period of transmission may advantageously be more often than UV sensors 21-24 so that the system can react more quickly to an emergency shutoff event. As such, time periods on the order of 1, typically 0.5 to 1.5, seconds are recommended, but not required. Similar to UV sensors 21-24, the transmission time could be selected to be a prime number around 1 second to avoid periodic radio frequency (RF) transmissions with the UV sensor group as previously discussed.

Central computer 11 may also be timing the receipt of the messages from door sensor 30. Should central computer 11 not receive a message from door sensor 30 within some maximum time duration, it will shut down the system so that the operator can determine the cause of the loss of door sensor 30 messages. A system malfunction or a discharged battery may be probable causes.

Another system related issue has to do with the identification of UV sensors as opposed to door sensors. Each sensor may have a unique identification number assigned to it. A rule may be used to easily identify the distinction between a UV sensor and a door sensor. A preferred embodiment uses even identification numbers for the door sensors and odd identification numbers for the UV sensors. However, other coding schemes are not precluded. For example, the UV sensors and door sensors may be associated with any emitter network under central computer command.

An integral part of the sterilization system is the data logging and reporting performed by central computer 11 as shown in FIG. 1. Data logging provides various capabilities to this system, such as recording door open/close events, recording pause/resume events, recording configuration changes, and providing auditing based upon what user is using the system, what he does, and how effectively rooms are disinfected. Further, electricity usage may be monitored in order to detect lamp or ballast failures.

Upon commencing a disinfection job, a data record is created indicating the location being treated and start time. This record is kept in central computer 11, and a copy is transmitted and posted on a secure web server with access only by authorized users with valid access information including a password. Once the first set of UV sensor readings are received by the computer, the estimated time to completion is calculated by the computer based upon the target dosage and the actual incident intensity measurements. An update is then made to the job data record which includes the latest sensor readings, estimated time to completion, and elapsed time. Other data items including starts and stops, job termination, patient identification numbers, and pathogen being treated for are tracked and reported as well. A unique benefit of this reporting system is the ability for sharing of real-time data among different departments of the facility using the system. In the case of a hospital, the admitting department will benefit from such reporting by having the ability to plan when to send patients to a room based upon the estimated job completion time. Or the cleaning department manager can use the real-time data to locate an employee and track their productivity. The infection prevention department may configure reports to aid in determining the efficacy of their disinfection protocol and to track problem patients or areas of their facility. There are other benefits to real-time access to job data and they are not precluded. An additional feature is the ability to post jobs to be performed to this system via a remote web server. That feature affords interested departments the ability to plan and schedule resources and to plan patient room assignments.

The system employs an Internet Protocol address sharing scheme which enables two or more wireless devices shown in FIG. 1, central computer 11 and remote control 40, the ability to communicate with each other inside or behind a firewall. Typically, the devices acquire an IP address dynamically from the hosting DHCP server so none of the devices can predict the address of any other device. The devices are capable of communicating with the Internet through the firewall, but their local network addresses are translated as their messages are sent out to the Internet. The firewall does not accept incoming traffic except in response to an outbound message.

There is no local name-server in which the devices can store their names and network addresses. The problem becomes a question of how the devices find each other so they can communicate. Within the present disclosure, this may be solved by having central computer 11 capture and send its local untranslated IP address to a remote Internet host. As the message is sent, the address of central computer 11 is translated (encapsulated) by the firewall, but the message payload contains the local untranslated IP address given by the DHCP server inside the firewall. Remote control 40 contacts the remote Internet host and reads the local untranslated IP address of the computer 11. Remote control 40 can now directly contact central computer 11 using the local untranslated IP address on the local network inside the firewall. Although the Internet host is outside the firewall and cannot use the untranslated address directly, it can store the address that is scoped to the inside-the-firewall devices. Other inside-the-firewall devices can use the Internet host as name-server for local addresses.

In addition to allowing these devices the ability to communicate with each other, the host facility's firewall automatically blocks all attempts to communicate with them from devices located outside the firewall. All addresses are automatically updated to the remote Internet host any time a new IP address is obtained.

The central computer of the present disclosure may include its own web server, which may be accessed remotely. This allows an authenticated remote user to access local data and even remotely control the system.

In some embodiments, the devices may communicate with the Internet via a wireless telephone network (e.g., a cellular network). This may be advantageous in situations where it is not desirable to rely on the Internet connectivity of the facility.

The Internet connection, in whatever form, is also useful for such purposes as job reporting, remote system configuration, data backup, diagnostics, and remote operation.

Figure 2:
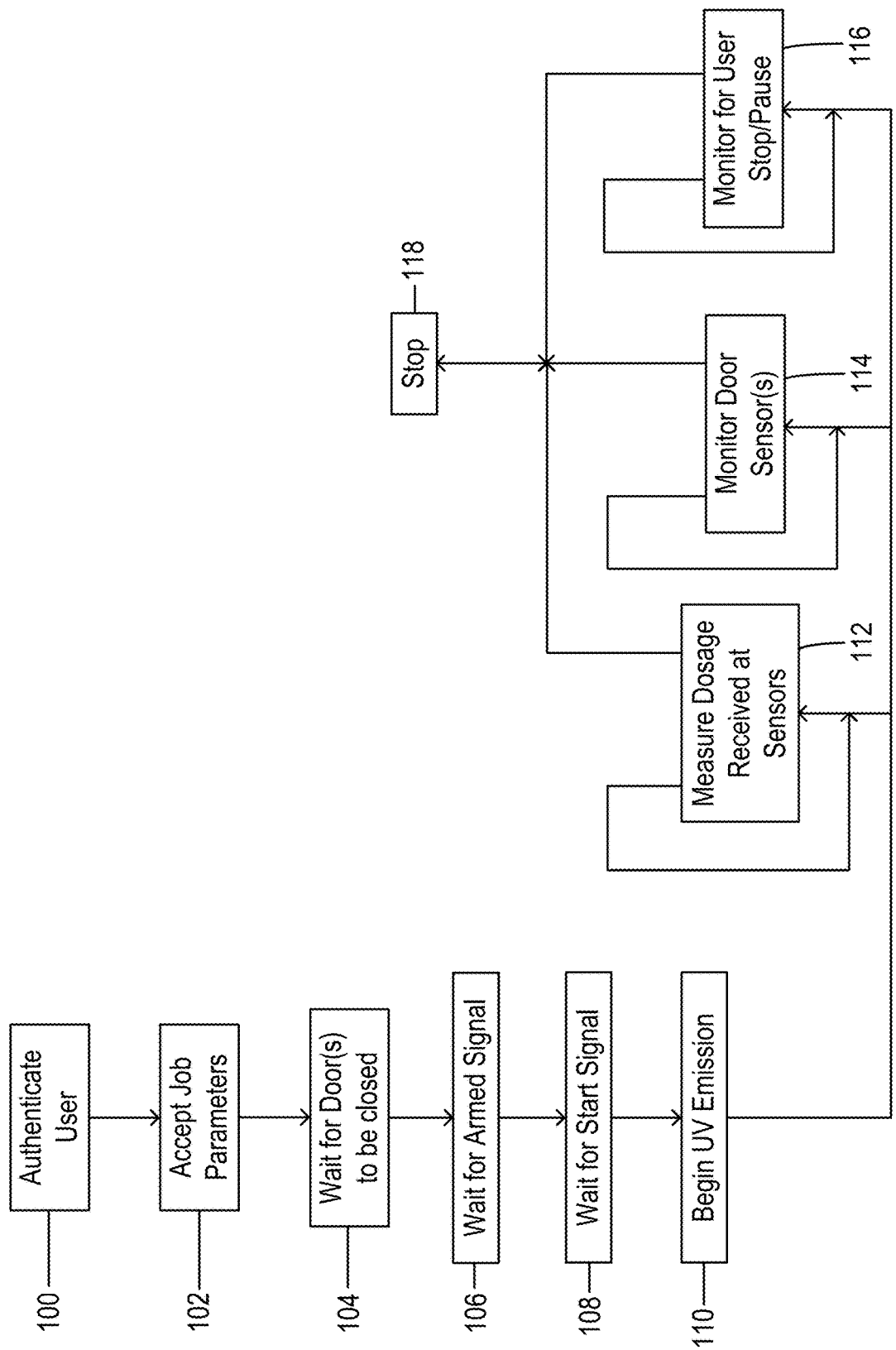
FIG. 2 is a process flow of a method of using the disinfection system, in accordance with the present invention.

FIG. 2 presents a flowchart of one embodiment of how a device according to the present disclosure may be operated. At step 100, the user is authenticated via username and password, or any other suitable authentication means, at the remote control (or via an on-site or off-site computer).

At step 102, the user selects various job parameters to configure the system. These parameters may include such items as a name or numerical designator for the room/area being disinfected, a desired UV dosage based on the disinfection level desired and the pathogen(s) to be killed, and what set of peripherals to use in the cleaning. These peripherals include things like the door sensor(s) and UV sensor(s).

At steps 104, 106, and 108 the system waits for the door closed signal(s), armed signal, and start signal to occur, in order. Then at step 110, UV irradiation commences.

While the UV irradiation is in process, the system undergoes three loops: measuring the dosage received at the sensors 112, monitoring the door sensor 114 (which includes the emergency stop button on the door sensor), and monitoring for a user stop/pause instruction 116. When any of these monitoring loops detects its condition, UV irradiation is ceased. The three monitoring loops may advantageously occur at different frequencies. For example, the door monitoring loop is a safety concern, so it may be advantageous for it to occur at a higher frequency than the dosage monitoring loop. The user stop/pause monitoring loop may or may not be implemented as a listening loop; alternatively, it may simply be a command from the user that directly interrupts the UV irradiation. All of these embodiments are within the scope of the present disclosure.

FIGS. 3-11 show screenshots of some of the screens that may be displayed on the remote control of the present disclosure. In the embodiment shown, this software is running on Apple iOS. However, the remote control may provide the same or similar functionality through any of a variety of software platforms.

Figure 3:
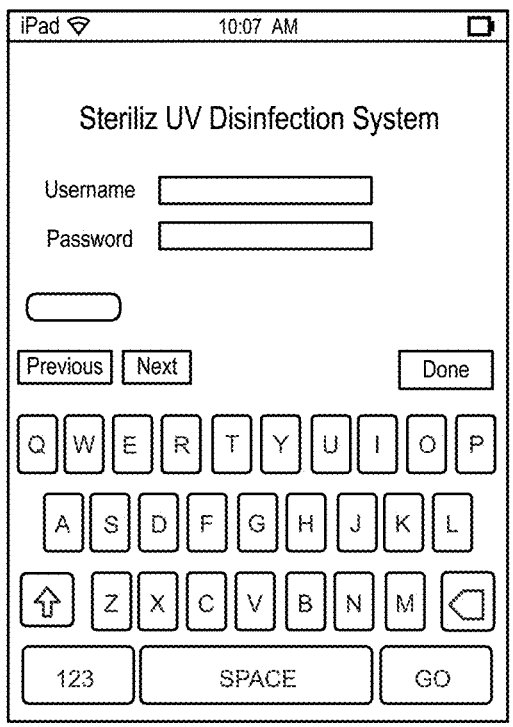
FIGS. 3-12 are screenshots of a remote operating device, in accordance with the present invention.
Figure 4:
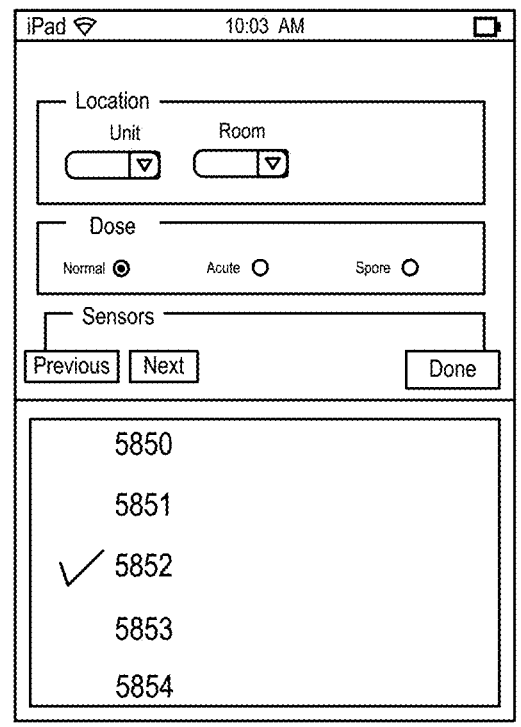

FIG. 3 shows a Login screen, allowing a user to authenticate via username and password. FIG. 4 shows a Disinfect screen that allows the user to select the Unit, the room being cleaned, and the dosage desired. Rooms may be pre-programmed into the system for easy logging and auditing of cleaning procedures and then selected via drop down menus. One embodiment includes automatic position detection, via GPS, inertial positioning, Wi-Fi triangulation, or other suitable methods. The logging of treatment records allows 2D/3D visualizations of things such as untreated areas, areas with high treatment frequency, etc.

Figure 5:
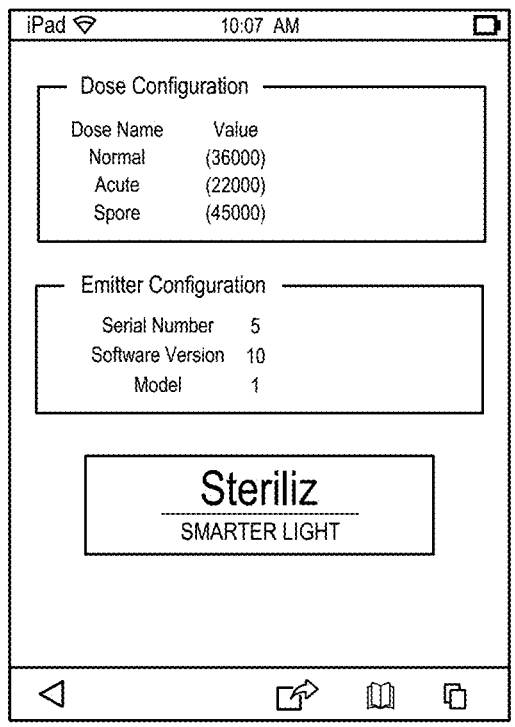
Figure 6:
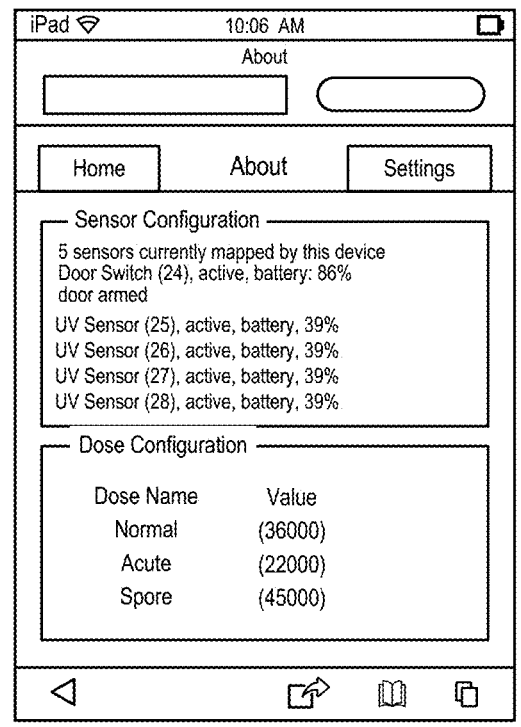

FIG. 5 shows the dose and emitter configuration. FIG. 6 shows an About screen, which lists the active sensors and their battery states.

Figure 7:
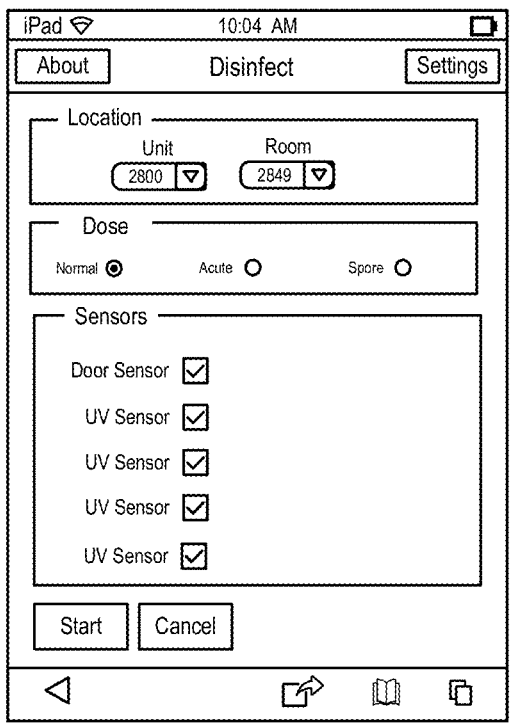

FIG. 7 shows the Disinfect screen, ready to start. At least one UV sensor must be enabled in order for the system to operate.

Figure 8:
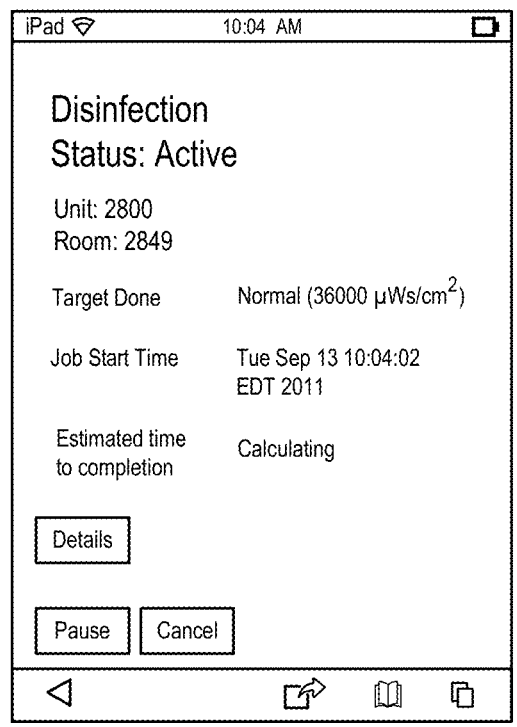

FIG. 8 shows a Status page listing the parameters of the disinfection job and the estimated time to completion, which the system may calculate based on the UV light levels observed at the UV sensors.

Figure 9:
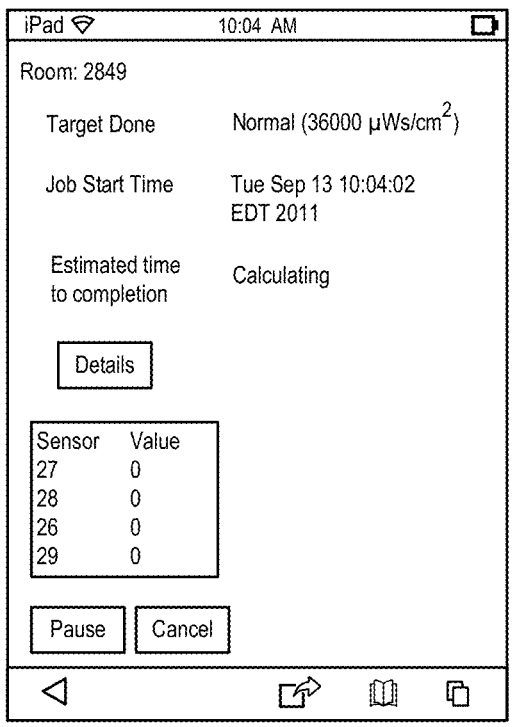

FIG. 9 shows the detail view available in FIG. 8, demonstrating the levels observed at each sensor.

Figure 10:
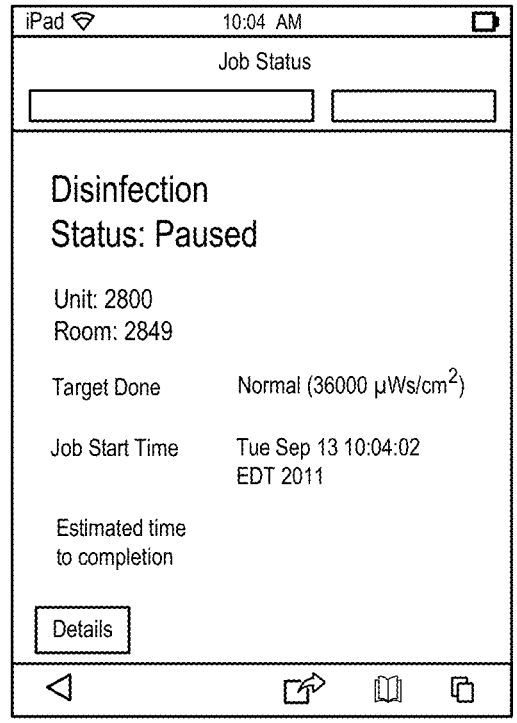
Figure 11:
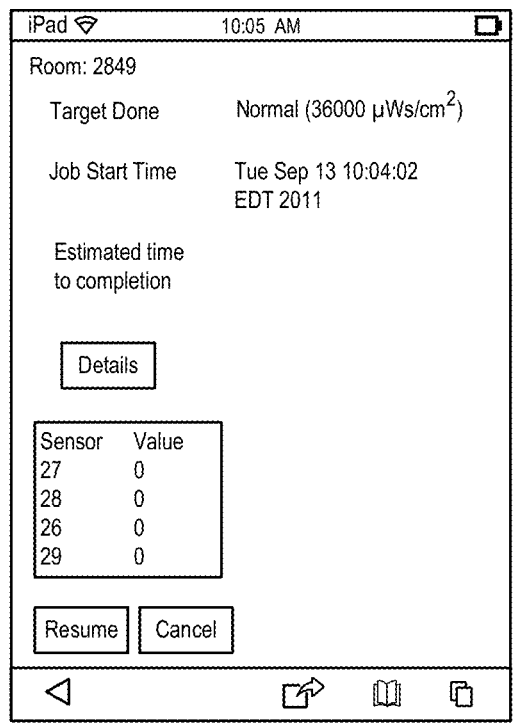
Figure 12:
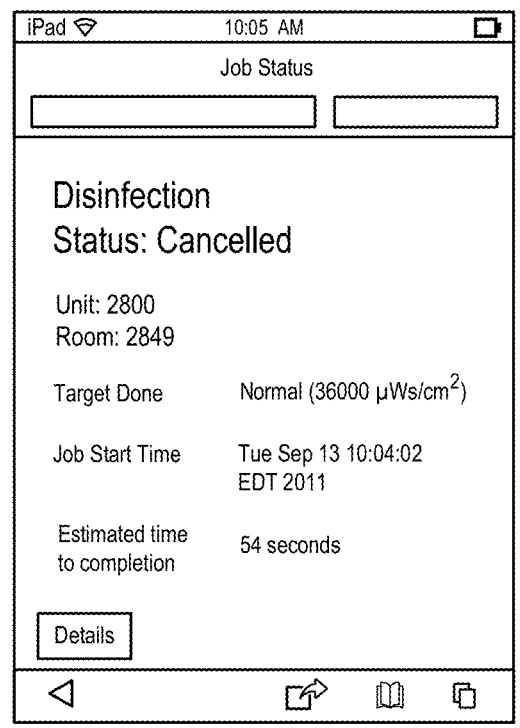

FIG. 10 shows the Status screen of a paused disinfection job, and FIG. 11 shows the option to resume or cancel the paused job. The job may be paused or canceled at any time by the operator via the remote control, so long as there is network connectivity between the remote control and the emitter. If connectivity is lost, the job may be stopped by pressing the emergency stop switch on the door safety sensor. FIG. 12 shows the Status page for a job that has been canceled.

Figure 13:
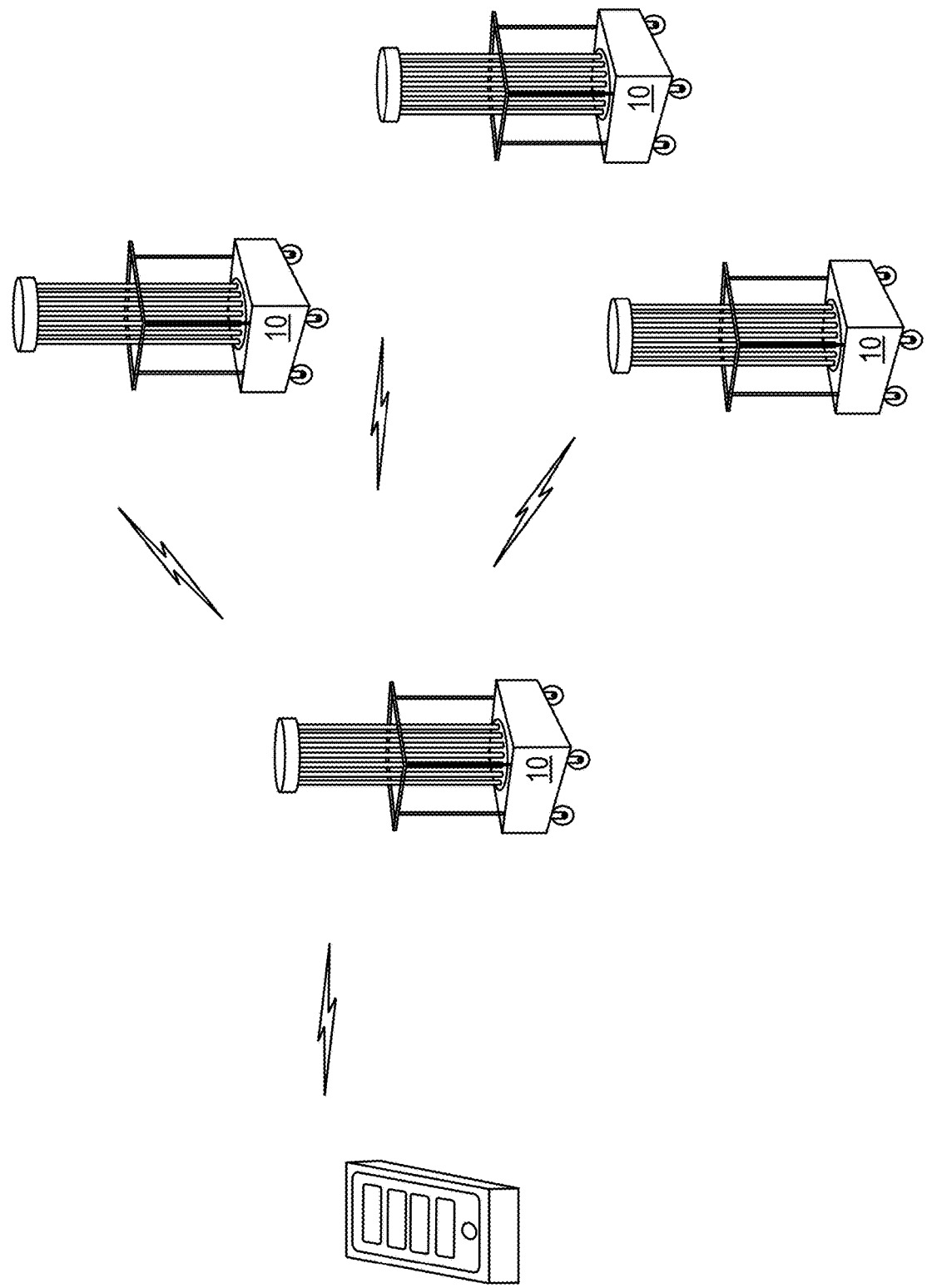
FIG. 13 is a perspective view of a preferred embodiment of the present invention, including a Master UV emitter transmitting signals to three Slave emitters.
Figure 14:
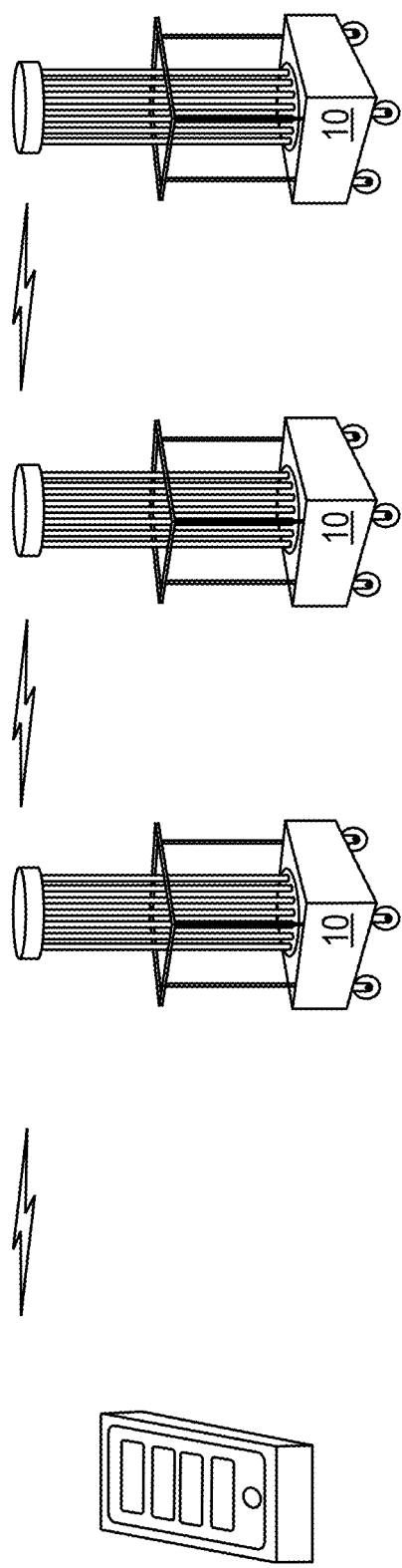
FIG. 14 is a perspective view of a preferred embodiment of the present invention, similar to the embodiment of FIG. 13, including a Master UV transmitting a signal to a first slave UV emitter, which is rebroadcasting the signal to a second slave UV emitter out of range of the Master UV emitter.

A preferred embodiment of the present invention broadly embodied in FIGS. 13 and 14 includes a multiple emitter configuration, with a Master emitter 10a, and plural Slave emitters 10b.

The remotely located control station for operation of this system is in data communication with only the Master emitter 10a. The multiple Slave emitters 10b are not in data communication with the control station. The Slave emitters 10b are separately in data communication only with the Master emitter 10a, not with the control station. With this embodiment many Slave emitters 10b may be located within a large space to be disinfected and by employing a repeater technique, the distance limitation is eliminated. The repeater technique employed may be of several different types. The preferred embodiment utilizes a simple repeat of a received radio frequency signal one time by each emitter that receives the signal. In this design a quasi-mesh network is established. There is no back-and-forth signal transmission between the Slave emitters 10b. When a Slave emitter 10b receives a signal meant for another Slave emitter 10b, not for itself it simply re-broadcasts it. In this way a Slave emitter 10b located out of range of the Master emitter 10a will receive a message intended for it through the process of the Slave emitters 10b sequentially re-broadcasting the message one time until the Slave emitter 10b for which the message is intended receives it.

The present invention is capable of detecting and correcting a potential overload condition. The preferred embodiment utilizes a voltage drop monitoring scheme. When the Master emitter 10a is fully energized it measures the AC voltage to which it is connected, and the AC current it is drawing. The Master emitter 10a then sends a message to one of the Slave emitters 10b instructing it to begin energizing its lamps. If the Master emitter 10a measures a significant subsequent drop in voltage or increase in current, it indicates a potential that two emitters are plugged into the same circuit, posing an overload condition. In such an event the Master emitter 10a will transmit a signal to the Slave emitter 10b instructing it to turn its lamps off and not participate in the current disinfection job. This process is repeated for each Slave emitter 10b as it begins to energize its respective lamps. Each already energized emitter will participate in the monitoring scheme and advise as needed.

The present invention incorporates many other features to ensure safe and reliable operation. These features include, but are not limited to the following:

A password-protected remote control, which will only operate the system after a valid user name and password has been entered, prevents unauthorized use of the device.

A fail-safe lamp operating time limit also prevents damage to the lamps and overexposure of the room being treated. The present invention includes a built-in timer limiting the "on time" for a treatment cycle. This may come initially programmed to limit the maximum lamp "on time" to approximately one hour. It may be changed to any amount of time up to, for example, two hours by an authorized service technician. In the unlikely event of a computer failure, the built-in timer will turn off the lamps after the lamps have been on for the programmed amount of time, even if the job hasn't completed.

The present invention also may incorporate an internal circuit breaker that will turn off all power to the system in the unlikely event of an overload that is not protected by the facility's circuit protection system. In some embodiments, this may be a 20 amp time delay circuit breaker. This circuit breaker must be manually reset by a qualified technician. To protect against fires and thermal damage, the system may include an internal temperature sensor that will turn off all power in the event the internal temperature of the lower electronics cabinet is at or above the designed temperature limit.

The present invention also may be equipped with a battery conservation system that automatically turns off power to on-board battery-operated devices (including chargers for remote sensors, cooling fan, and computer) when it has not been plugged into facility electrical power for a period of time. It is recommended that the device be plugged into facility electrical power when not in use.

The UV emitters 10 may be equipped with two wheels that have push down brakes which, when depressed and locked into place, prevent them from rotating and spinning. The other two wheels are free to rotate and spin. They may be locked such that they can only spin and not rotate, like the rear wheels on a shopping cart.

Figure 15:
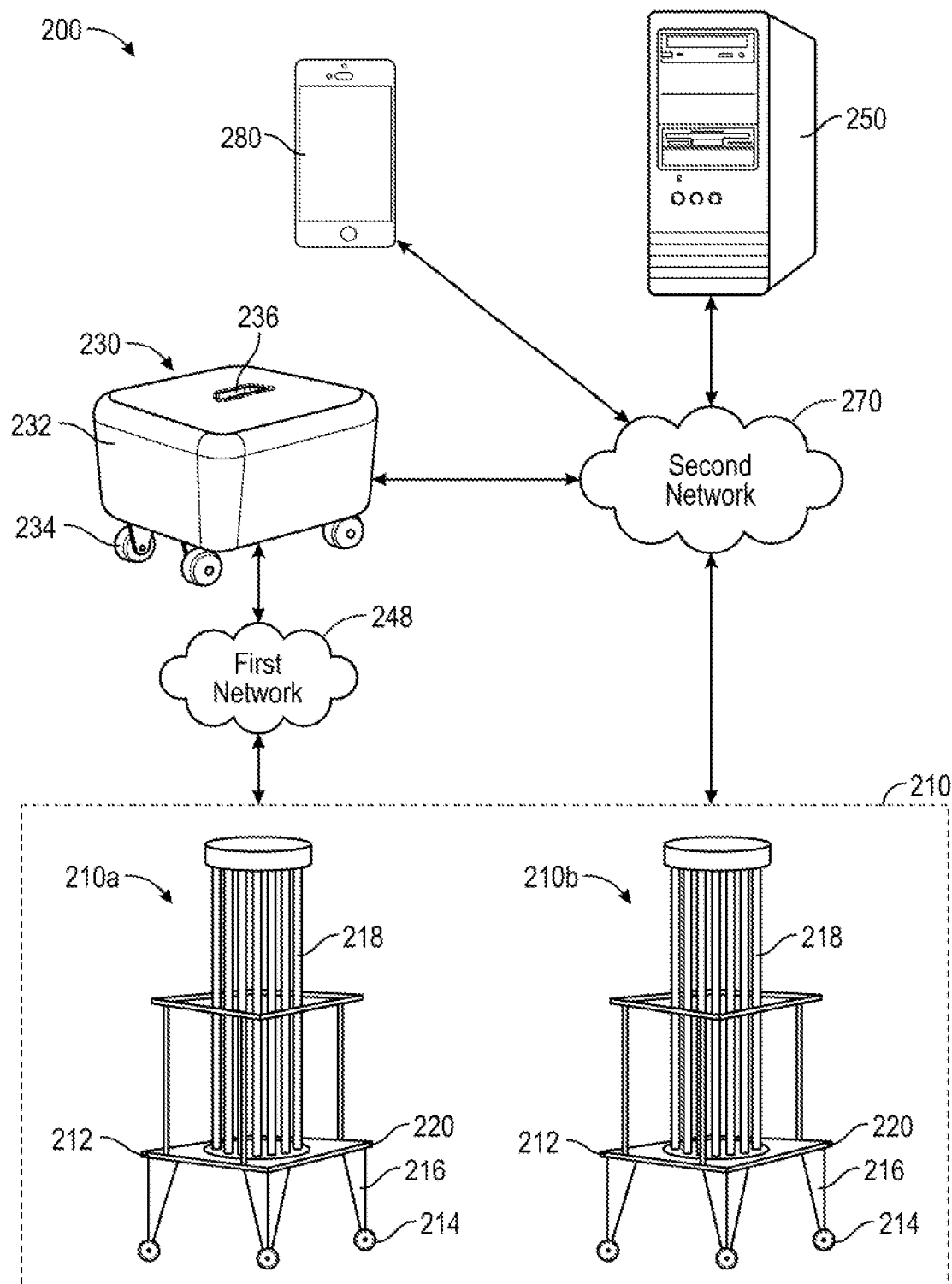
FIG. 15 illustrates an environment in which sterilization system is implemented, in accordance with one embodiment of present invention.
Figure 16:
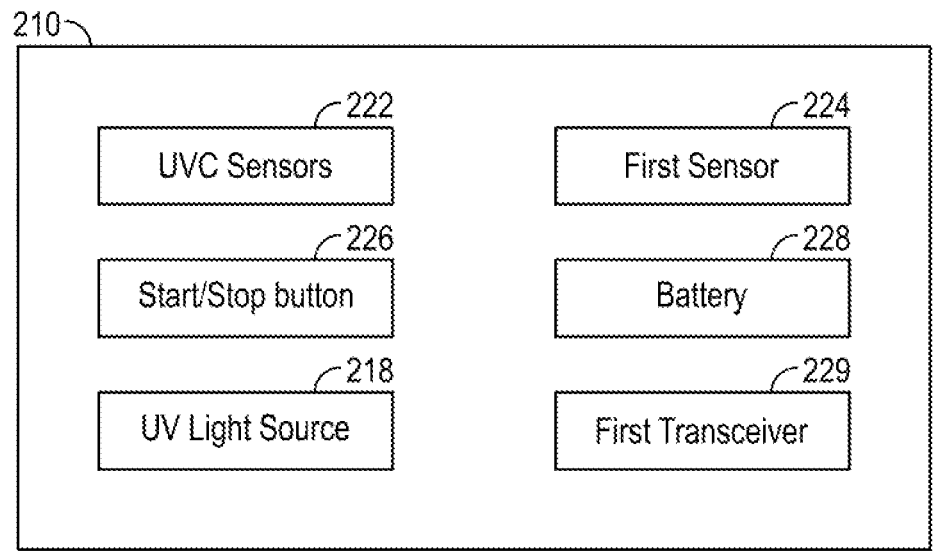
FIGS. 16 through 19 illustrate block diagrams of Ultraviolet (UV) emitter module, robotic system, server and user device, respectively.

In one embodiment, the present invention discloses a sterilization system for improving duty cycle of robotic system and Ultraviolet (UV) emitter modules disinfecting closed environment. FIG. 15 shows an environment in which sterilization system 200 is used, in accordance with one embodiment of the present invention. Sterilization system 200 includes plurality of UV emitter modules 210, e.g., first UV emitter module 210a, second UV emitter module 210b and so on, collectively referred as UV emitter modules 210. Each of UV emitter modules 210 includes base 212. Base 212 may be made of suitable material and may be used for placing Ultraviolet (UV) light source 218. Base 212 may be provided with wheels 214 via caskets or support frames 216. Further, UV emitter module 210 may include UV light source 218. UV light source 218 may indicate a UV germicidal bulb that emits very short ultraviolet wavelengths from 100 to 280 nanometers that damages the Deoxyribonucleic Acid (DNA) of bacteria, viruses, and other pathogens. Further, UV emitter module 210 includes housing 220 provided at base 212. Housing 220 may include one or more Ultraviolet C (UVC) sensors 222 (FIG. 16) configured for measuring power or intensity of incident UV radiation. Further, housing 220 may include first sensor 224. First sensor 224 may include, but not limited to, an image sensor, infrared sensor, laser sensor, motion sensor configured to detect the presence of humans in the vicinity of UV emitter module 210. In one embodiment, UV emitter module 210 may comprise start/stop button 226 provided at outer side of housing 220 allowing user to operate UV emitter 210. Further, UV emitter module 210 may include battery 228 for powering UV light source 218. In the current embodiment, UV emitter module 210 may include first transceiver 229 for transmitting or receiving signals from external devices such as motorized base or robotic system 230, or server 250, or user device 280.

Sterilization system 200 includes robotic system 230 communicatively connected to UV emitter module 210 via first network 248. Robotic system 230 includes housing 232 made of variety of material such as metal, plastic or any other suitable material. Housing 232 may be provided in a variety of shapes such as square, rectangular or any other shape. Housing 232 includes wheels 234 provided at the bottom for maneuvering robotic system 230 over surface or ground. Further, robotic system 230 includes emitter interface 236 configured for connecting robotic system 230 to UV emitter for transporting and charging battery 246 via UV emitter module 210.

Figure 17:
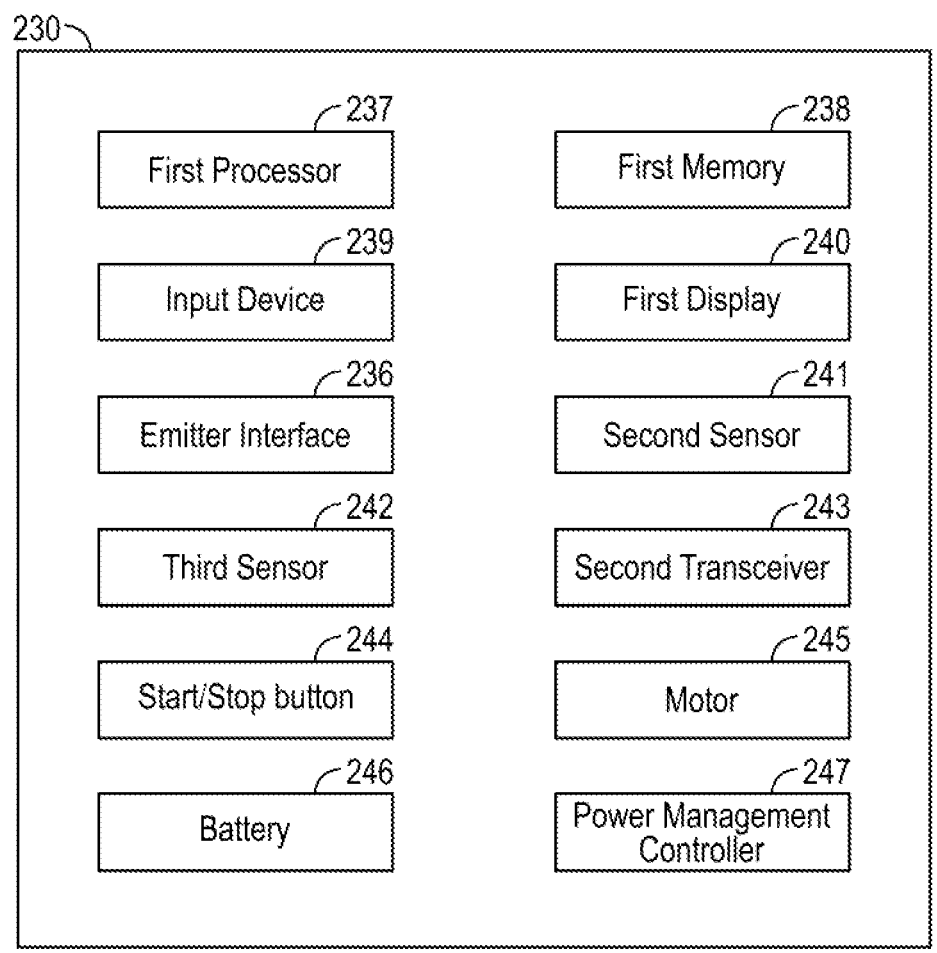

FIG. 17 shows a block diagram of robotic system 230. Robotic system 230 includes first processor 237, first memory 238, input device 239, first display 240, second sensor 241, third sensor 242, second transceiver 243, start/stop button 244, motor 245, battery 246, and power management controller 247.

First processor 237 includes central processing unit (CPU), graphics-processing unit (GPU) or both. First processor 237 may include any suitable processing device, such as microprocessor, microcontroller, integrated circuit, logic device, or other suitable processing device.

First memory 238 communicates with first processor 237 via bus (not shown). First memory 238 may include one or more computer-readable media, including, but not limited to, non-transitory computer-readable media, RAM, ROM, hard drives, flash drives, or other memory devices. First memory 238 may store information accessible by first processor 237, including computer-readable instructions that may be executed by first processor 237. In one example, first memory 238 may be used to store data that may be retrieved, manipulated, created, or stored by first processor 237.

Instructions can be any set of instructions that when executed by first processor 237, cause first processor 237 to perform certain operations. Instructions may also reside, completely or at least partially, within first memory 238 and/or within first processor 237 during execution thereof by robotic 230, first memory 238 and first processor 237 also constituting machine-readable medium. Instructions may further be transmitted or received over first network 238 or second network 270 via second transceiver 243 utilizing one of several well-known transfer protocols or custom protocol.

Input device 239 includes keyboard/keypad, or touch screen used for providing an input to robotic system 230.

First display 240 includes a device used for displaying data in the form of text/video to users.

Second sensor 241 may include image sensor configured to detect or capture presence of users or objects in vicinity of robotic system 230 or within closed environment. In one example, second sensor 241 may include optical, infrared, or laser detection sensor configured to detect position or motion or movement of users in the vicinity of robotic system 230.

Third sensor 242 may include location or position sensor configured for determining location of robotic system 230. In one example, third sensor 242 may include Global Positioning System (GPS) sensor.

Second transceiver 243 sends and receives data from robotic system 230 to other devices such as UV emitter module 210, server 250, or user device 280 via first network 248 or second network 270.

Start/stop button 244 includes a physical button provided at outer surface of housing 232 or soft touch button provided on first display 240. Start/stop button 244 may be configured to power ON or power OFF robotic system 230.

Motor 245 may include DC motor configured to drive wheels 234 when instructed by first processor 237.

Battery 246 acts as a power source for operating motor 245 or various components of robotic system 230. Battery 246 may include standalone rechargeable battery or battery having an electric cord plugged to energy source (AC/DC).

Power management controller 247 includes a scheme or set of instructions configured to enable robotic system 230 to turn OFF itself when not used for a predetermined time period for reducing dynamic power consumption of battery 246. Further, scheme is configured to re-enable robotic system 230 with a fast wake-up time of less than e.g., 1 millisecond (ms), when the user presses start/stop button 244.

Although it is shown that housing 232 includes second sensor 241 and third sensor 242, person skilled in the art will appreciate that second sensor 241 and third sensor 242 may be provided at outer side of housing 232 to capture presence of users or to detect location of robotic system 230 and transmit signals to first processor 237 for processing the data sensed by second sensor 241 and third sensor 242.

As specified above, UV emitter module 210 is communicatively connected to robotic system 230 via first network 248. First network 248 may include a short-range wireless network such as Bluetooth, ZigBee, Radio-frequency Identification (RFID), beacons, Near Field Communication (NFC) and so on. Alternatively, first network 248 may include wireless network, wired network or combination thereof. First network 248 may be implemented as one of the different types of networks, such as intranet, local area network (LAN), wide area network (WAN), the internet, and the like. First network 248 may either be a dedicated network or shared network. Shared network represents an association of the different types of networks that use variety of protocols, for example, Hypertext Transfer Protocol (HTTP), Transmission Control Protocol/Internet Protocol (TCP/IP), Wireless Application Protocol (WAP), and the like, to communicate with one another.

Figure 18:
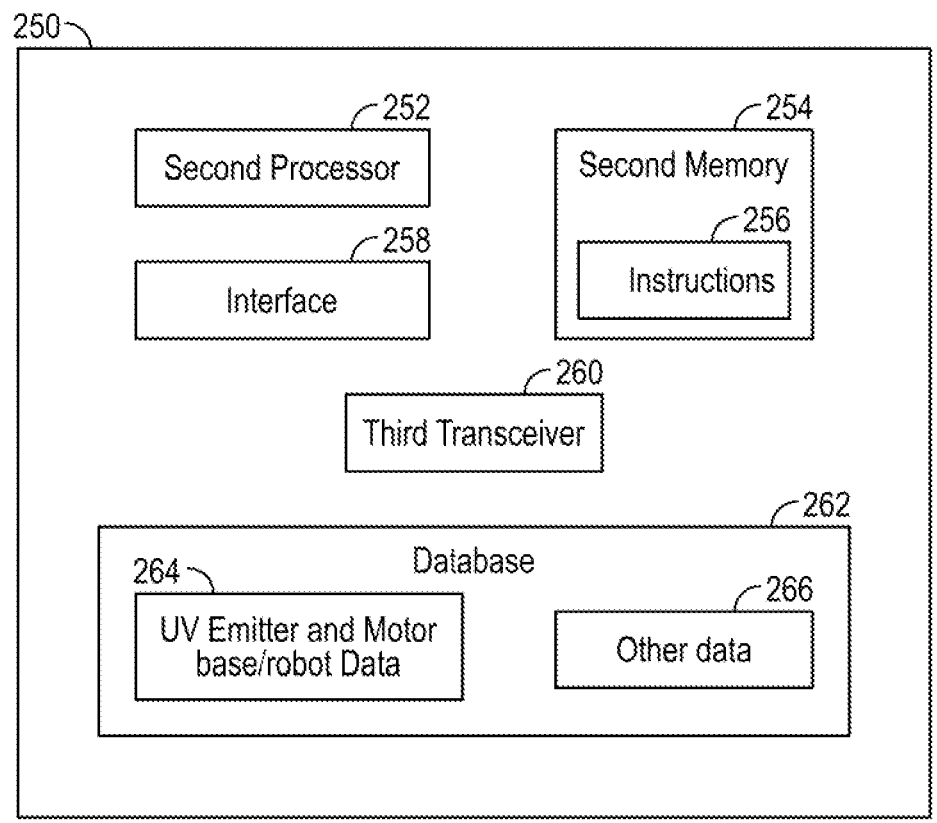

Further robotic system 230 is communicatively connected to server 250 via second network 270. FIG. 18 shows a block diagram of server 250. Server 250 includes second processor 252 (e.g., central processing unit (CPU), graphics processing unit (GPU) or both. Server 250 includes second memory 254 which communicate with second processor 252 via bus (not shown).

Second processor 252 may include any suitable processing device, such as a microprocessor, microcontroller, integrated circuit, logic device, or other suitable processing device.

Second memory 254 may include one or more computer-readable media, including, but not limited to, non-transitory computer-readable media, RAM, ROM, hard drives, flash drives, or other memory devices. Second memory 254 may store information accessible by second processor 252, including computer-readable instructions 256 that can be executed by second processor 252. In one example, second memory 254 can be used to store data that can be retrieved, manipulated, created, or stored by second processor 252.

Instructions 256 can be any set of instructions that when executed by second processor 252, cause second processor 252 to perform operations. Instructions 256 may also reside, completely or at least partially, within second memory 254 and/or within second processor 252 during execution thereof by server 250, second memory 254 and second processor 252 also constituting machine-readable medium. Instructions 256 may further be transmitted or received over second network 270 via third transceiver 260 utilizing one of several well-known transfer protocols or a custom protocol.

Server 250 includes user interface (UI) 258 i.e., software or Application interface allowing the user of server 250 to interact with user device 280, UV emitter module 210 and robotic system 230.

Server 250 further includes third transceiver 260 configured to send and receive data from server 250 to other devices such as robotic system 230, user device 280 and UV emitter module 210.

Server 250 further includes database 252. Database 252 indicates data structure configured for storing the information. In the current embodiment, database 252 includes UV emitter and motor base or robotic system data 264, and other data 166. UV emitter and motor base or robotic system data 264 includes data corresponding to UV emitter module 210 and robotic system 230. For example, UV emitter and motor base or robotic system data 264 includes name, type, serial number or unique identification number, manufacturer, manufacturing date, model number, maintenance schedule, location, etc. of each of UV emitter modules 210 i.e., first UV emitter module 210a and second UV emitter module 210b and robotic system 230.

Second network 270 may include wireless network, wired network or combination thereof. Second network 270 can be implemented as one of the different types of networks, such as intranet, local area network (LAN), wide area network (WAN), the internet, and the like. Second network 270 may either be a dedicated network or shared network. Shared network represents an association of different types of networks that use variety of protocols, for example, Hypertext Transfer Protocol (HTTP), Transmission Control Protocol/Internet Protocol (TCP/IP), Wireless Application Protocol (WAP), and the like, to communicate with one another. Further, second network 270 may include variety of network devices, including routers, bridges, servers, computing devices, storage devices, and the like.

Figure 19:
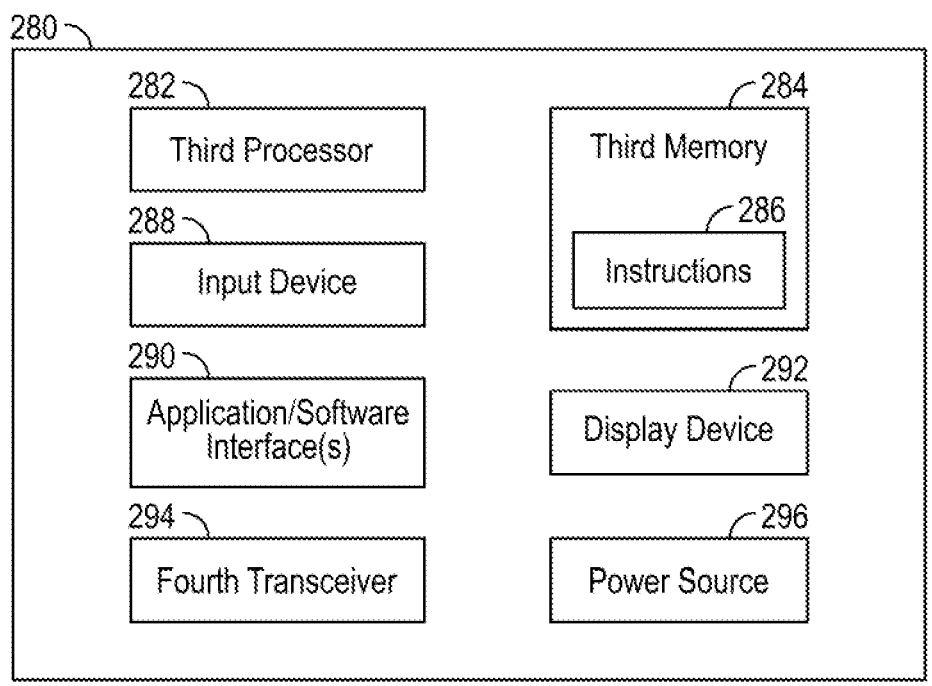

Further, robotic system 230 and UV emitter module 210 are further communicatively connected to user device 280 via second network 270. FIG. 19 shows a block diagram of user device 280. User device 280 may include mobile phone, laptop, desktop, tablet, smart watch and any other electronic device. User device 280 includes third processor 282 (e.g., central processing unit (CPU), graphics processing unit (GPU) or both. User device 280 includes third memory 284 which communicate with third processor 282 via bus (not shown).

Third processor 282 may include any suitable processing device, such as a microprocessor, microcontroller, integrated circuit, logic device, or other suitable processing device.

Third memory 284 may include one or more computer-readable media, including, but not limited to, non-transitory computer-readable media, RAM, ROM, hard drives, flash drives, or other memory devices. Third memory 284 may store information accessible by third processor 282, including computer-readable instructions 286 that can be executed by second processor 252. In one example, third memory 284 can be used to store data that can be retrieved, manipulated, created, or stored by third processor 282.

Instructions 286 can be any set of instructions that when executed by third processor 282, cause third processor 282 to perform operations. Instructions 286 may also reside, completely or at least partially, within third memory 284 and/or within third processor 282 during execution thereof by user device 280, third memory 284 and third processor 282 also constituting machine-readable medium. Instructions 286 may further be transmitted or received over second network 270 via fourth transceiver 294 utilizing one of several of well-known transfer protocols or a custom protocol.

User device 280 includes input device 288. Input device 288 includes keyboard/keypad, or touch screen used for providing an input to user device 280.

User device 280 includes Application or software interface allowing user of user device 280 to interact with UV emitter module 210, robotic system 230, and server 250.

User device 280 further includes display device 292 used for displaying data in the form of text/video to user of user device 280.

User device 280 further includes fourth transceiver 294 configured to send and receive data from user device 280 to other devices such as UV emitter module 210, robotic system 230, and server 250.

User device 280 further includes power source 296 such as a battery for powering various components of user device 280.

Figure 20:
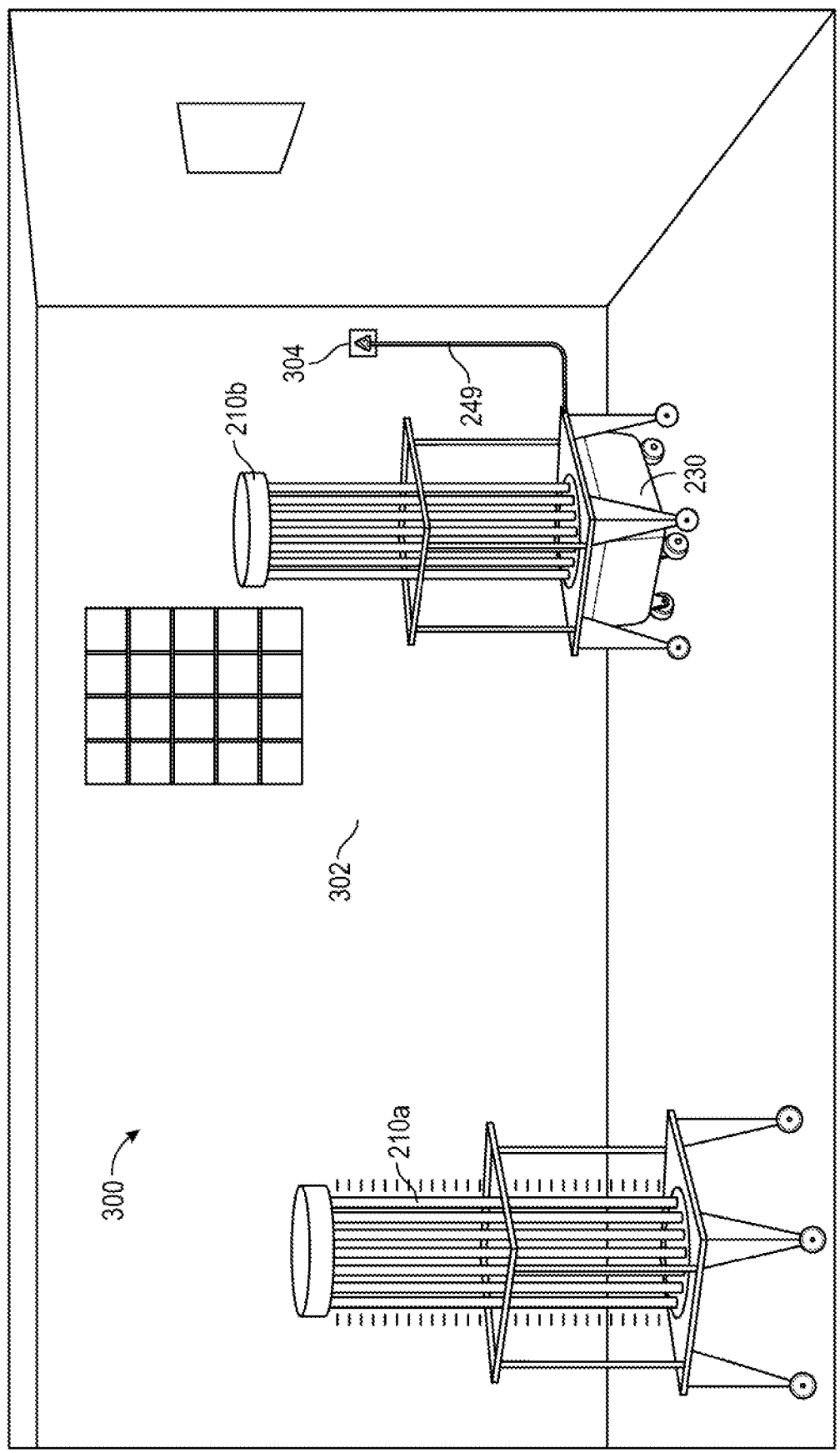
FIGS. 20 through 23 illustrate operational features of robotic system and UV emitter modules allowing 100% duty cycle of robotic system and UV emitter modules.

Now referring to FIGS. 15, and 20 through 23, the operational features and interaction of UV emitter module 210, robotic system 230, server 250 and user device 280 are explained. In accordance with one embodiment of the present invention, UV emitter modules 210 i.e., first UV emitter module 210a and second UV emitter module 210b may be used for sterilizing or disinfecting surfaces within closed environment 300 as shown in FIG. 20. In one embodiment, each of first UV emitter module 210a and second UV emitter module 210b may be provided with a unique identification number. Further, robotic system 230 may be configured to store unique identification number associated with first UV emitter module 210a and second UV emitter module 210b in first memory 238. Referring to FIG. 20, closed environment 300 such as a room, hospital or container where sterilization system 200 including separate UV emitter modules i.e., first UV emitter module 210a and second UV emitter module 210b, and robotic system 230 can be implemented is shown, in accordance with one exemplary embodiment of the present invention. Closed environment 300 may include wall 302 for mounting charging dock or power source 304. In the current embodiment, first UV emitter module 210a and second UV emitter module 210b, and robotic system 230 may be used as separate devices, each having their own resources such as battery for performing their respective operations. For example, consider battery 228 of first UV emitter module 210a is fully charged and being used for disinfecting interior or surface of closed environment. Further, consider battery 228 of second UV emitter module 210b is fully discharged. In accordance with current embodiment, robotic system 230 may mount second UV emitter module 210b via emitter interface 236 and maneuver second UV emitter module 210b to charging dock 304 as shown in FIG. 20.

In order to charge battery 228, each of first UV emitter module 210a and second UV emitter module 210b may be provided with cord 249 extending from housing 220. Alternatively, robotic system 230 may be provided with cord 249. When robotic system 230 mounted with second UV emitter module 210b reaches charging dock 304, cord 249 may be connected to charging dock 304 for charging second UV emitter module 210b as shown in FIG. 20.

Figure 21:
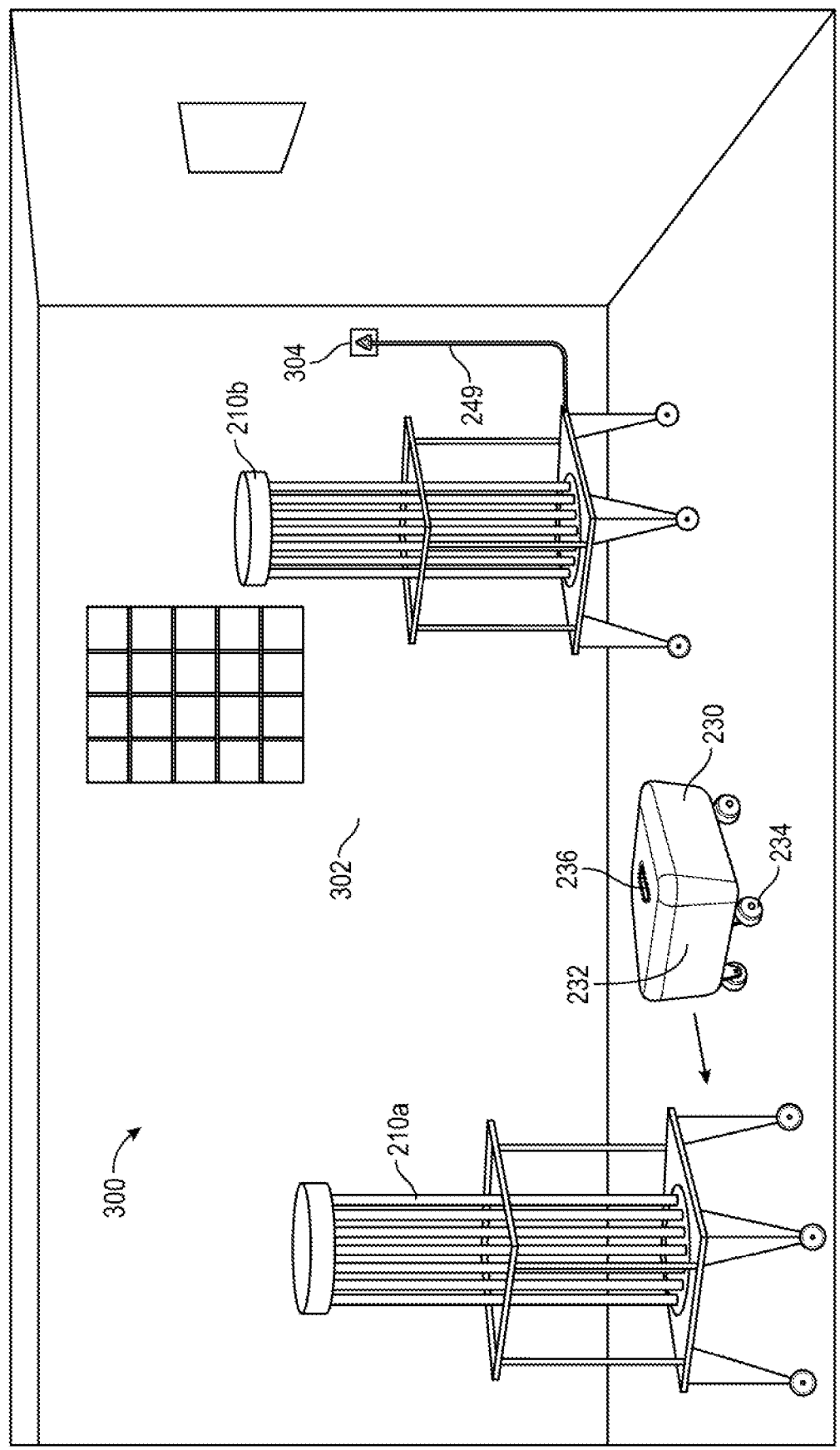

Now, consider that battery 228 of first UV emitter module 210a is fully discharged. In such a scenario, first UV emitter module 210a may transmit a signal indicating discharge of its battery 228. In the current embodiment, robotic system 230 may be configured to store location of each of first UV emitter module 210a, second UV emitter module 210b and charging dock 304 in first memory 238. As such, when first UV emitter module 210a transmits signal indicating discharge of battery 228, second transceiver 243 may receive the signal and send the signal to first processor 237. Subsequently, first processor 237 may employ emitter interface 236 to detach from second UV emitter module 210b and instruct motor 245 to maneuver wheels 234 to reach location of first UV emitter module 210a as shown in FIG. 21.

Figure 22:
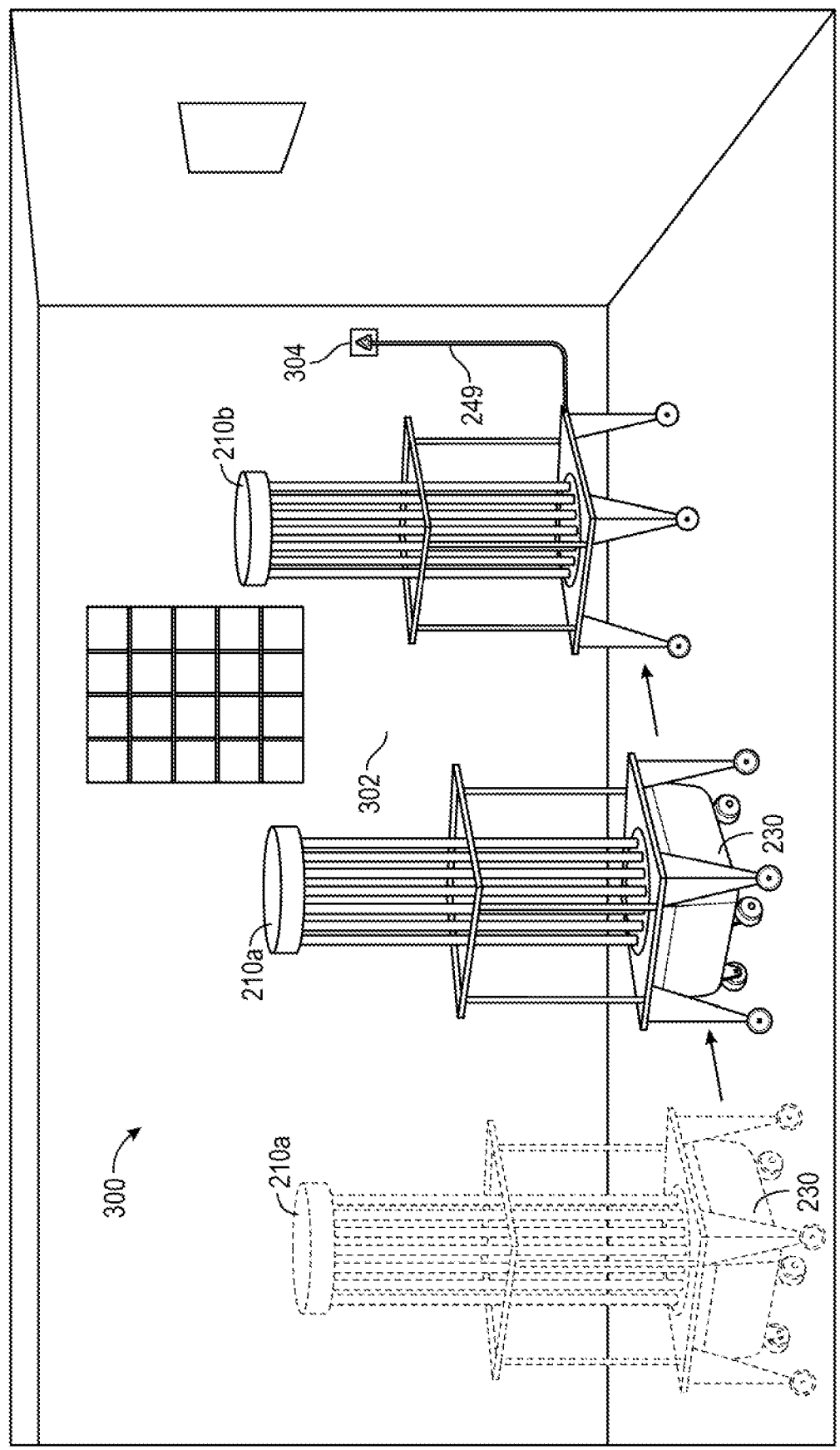

After reaching the location of first UV emitter module 210a, robotic system 230 may employ emitter interface 236 for mounting first UV emitter module 210a to robotic system 230. Subsequently, robotic system 230 may maneuver first UV emitter module 210a to reach charging dock 304 as shown in FIG. 22.

Figure 23:
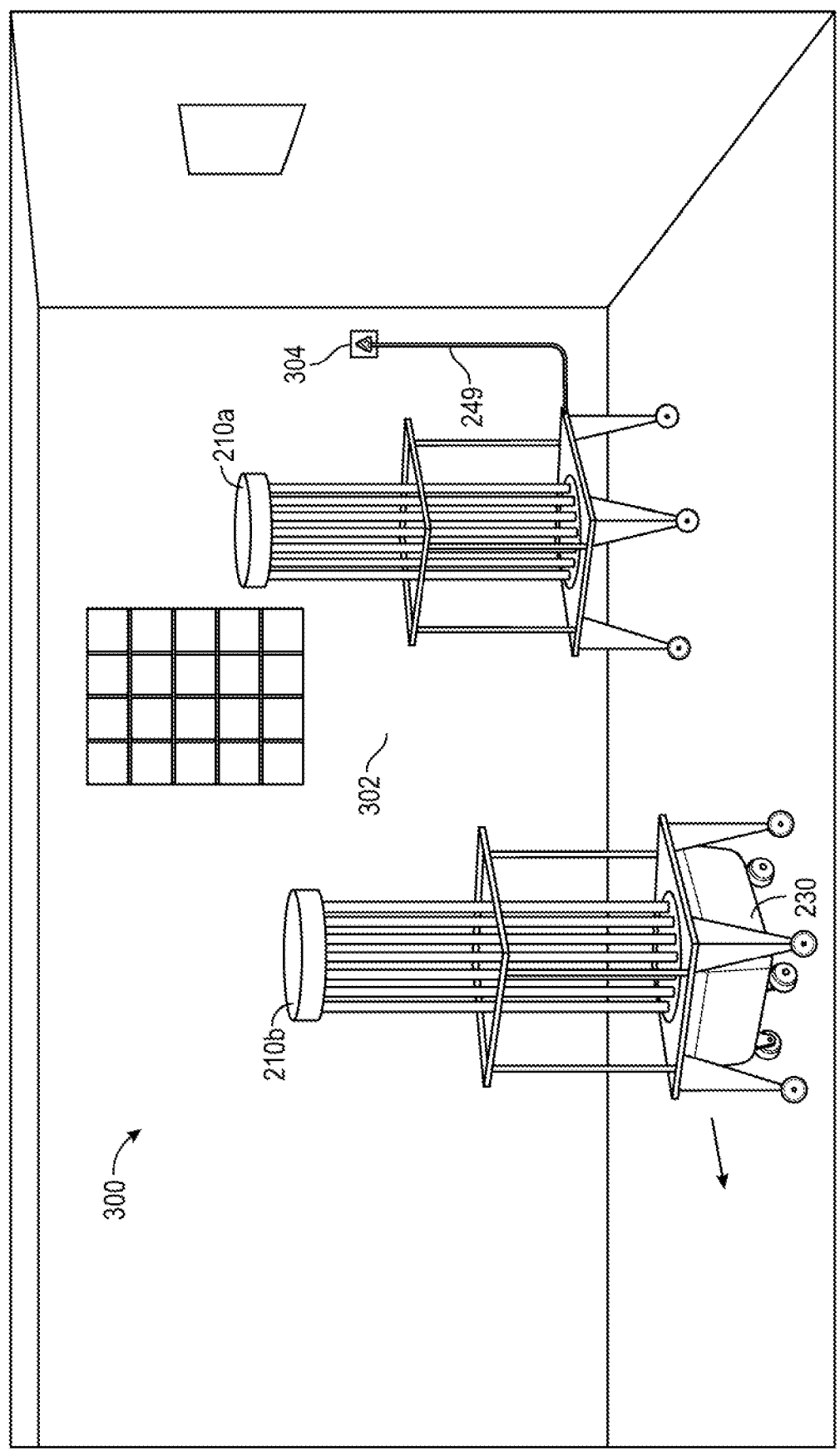

After reaching charging dock 304, robotic system 230 may demount first UV emitter module 210a and mount second UV emitter module 210b to move aside second UV emitter module 210b from charging dock 304. Subsequently, robotic system 230 may mount first UV emitter module 210a and maneuver closer to charging dock 304 for connecting cord 249 to charging dock 304 in order to charge battery 228 of first UV emitter module 210a, as shown in FIG. 23. After connecting first UV emitter module 210a to charging dock 304, robotic system 230 may mount second UV emitter module 210b and maneuver second UV emitter module 210b to a desired area or location (FIG. 23) within closed environment 300 where disinfection needs to be performed.

In accordance with one embodiment of the present invention, when second UV emitter module 210b is connected to charging dock 304 for charging battery 228 (FIG. 20), battery 246 of robotic system 230 may be charged through emitter interface 236. This way, both second UV emitter module 210b and robotic system 230 may be charged while first UV emitter module 210a is used for disinfecting closed environment 300. Similarly, when first UV emitter module 210a is connected to charging dock 304 for charging battery 228, battery 246 of robotic system 230 may be charged through emitter interface 236. This way, both first UV emitter module 210a and robotic system 230 may be charged while second UV emitter module 210b is used for disinfecting closed environment 300.

In another embodiment, battery 246 of robotic system 230 may be charged or recharged when robotic system 230 is transporting or maneuvering second UV emitter module 210b after charging battery 228 of second UV emitter module 210b, as shown in FIG. 23. Similarly, battery 246 of robotic system 230 may be charged or recharged when robotic system 230 is transporting or maneuvering first UV emitter module 210a after charging battery 228 of first UV emitter module 210a. This way, battery 246 of robotic system 230 may get charged continuously and be ready to transport UV emitter module 210 to charging dock 304 immediately after receiving signal indicating discharge of battery 228. In other words, battery 246 of robotic system 230 may get continuously charged or recharged from connected UV emitter modules 210, thereby allowing robotic system 230 and UV emitter modules 210 to have a 100% duty cycle. This ensures uninterrupted operation of robotic system 230 and UV emitter modules 210 for disinfecting closed environment 300 using UV emitter modules 210 and saves cost and manhours for users.

As specified above, robotic system 230 includes power management controller 247. In one implementation, power management controller 247 may be configured to turn OFF robotic system 230 after a hiatus, say 2 minutes of non-use or disconnection from UV emitter modules 210 to prolong life of battery 246. When one of first UV emitter module 210a and second UV emitter module 210b transmits signal corresponding to discharge of battery 228, then second transceiver 243 may receive the signal. Concurrently, power management controller 247 may turn ON robotic system 230. Subsequently, first processor 237 may employ third sensor 242 to detect location of first UV emitter module 210a or second UV emitter module 210b that transmitted signal corresponding to discharge of battery 228. It should be understood that robotic system 230 may employ first processor 237 to identify whether first UV emitter module 210a or second UV emitter module 210b has transmitted the signal using their unique identification number inferred from the signal. Consider that first processor 237 detects that second UV emitter module 210b transmitted signal indicating discharge of battery 228. Subsequently, robotic system 230 may employ third sensor 242 to detect the location of second UV emitter module 210b. After detecting the location, first processor 237 may employ second sensor 241 to detect presence of humans or objects in vicinity or path to reach the location of second UV emitter module 210b. Further, first processor 237 may employ motor 245 to maneuver wheels 234 to reach the location of second UV emitter module 210b. After reaching the location of second UV emitter module 210b, first processor 237 may employ emitter interface 236 to mount second UV emitter module 210b. Subsequently, first processor 237 may employ first sensor 241 and second sensor 242 to maneuver robotic system 230 mounted with second UV emitter module 210b to charging dock 304, as explained above with the help of FIGS. 20 to 23.

In one exemplary embodiment, robotic system 230 may be pre-configured to maneuver to one of first UV emitter module 210a and second UV emitter module 210b and transport to charging dock 304 for charging battery 228 at pre-determined time intervals, and subsequently to pre-defined area to disinfectant or sterilize using UV light source 218. Considering that battery 228 of first UV emitter module 210a takes about 30 minutes to charge fully and takes one (1) hour to discharge battery 228 when used for operating UV light source 218 for disinfecting, then robotic system 230 may be configured to maneuver to first UV emitter module 210a at every one hour thirty minutes to take it to charging dock 304 for charging battery 228 and subsequently to pre-defined area for disinfecting the pre-defined area. Similarly, the robotic system 230 may be pre-configured to maneuver second UV emitter module 210b to charging dock 304 for charging battery 228 at pre-determined time intervals and then maneuver to pre-defined locations.

In another embodiment, user of user device 280 may provide instructions to robotic system 230 to mount and maneuver one of the first UV emitter module 210a and second UV emitter module 210b to charging dock 304. Similarly, user device 280 may be used to instruct robotic system 230 to mount and maneuver one of the first UV emitter module 210a and second UV emitter module 210b from charging dock 304 to a desired area for disinfecting closed environment 300. In accordance with current embodiment, user of user device 280 may be able to selectively instruct robotic system 230 to maneuver one of the first UV emitter module 210a and second UV emitter module 210b for charging them or disinfecting closed environment 300. In one example, first UV emitter module 210a and second UV emitter module 210b may be provided in different sizes. For instance, first UV emitter module 210a may be provided in a smaller configuration than second UV emitter module 210b. In another example, first UV emitter module 210a and second UV emitter module 210b may be provided different UV frequency such as UV-C or far-UV or even alternative disinfection technology such as an electrostatic fogger. As such, user may use user device 280 to selectively instruct robotic system 230 to maneuver one of first UV emitter module 210a and second UV emitter module 210b to disinfect different areas in closed environment 300. For example, user may use user device 280 to selectively instruct robotic system 230 to maneuver first UV emitter module 210a to disinfect areas such as corners of closed environment 300. This way, the user may use robotic system 230 to return a discharged UV emitter module to a charging dock and leave it there to charge and immediately pick up a fully charged UV emitter module and return to desired area for disinfecting surface, thereby improving overall duty cycle of robotic system and UV emitter modules.

Figure 24:
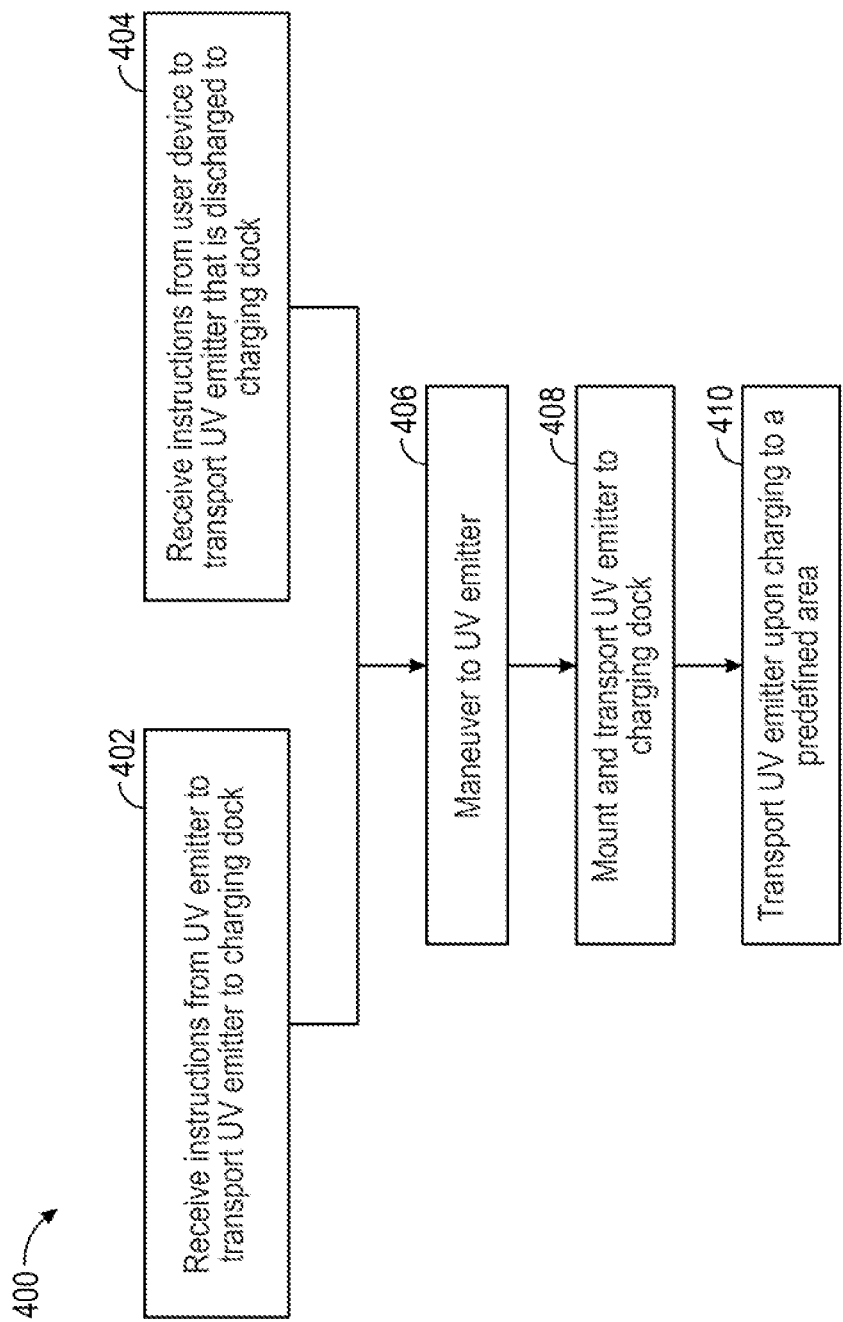
FIG. 24 illustrates a method implemented by robotic system, in accordance with one embodiment of present invention.

Now referring to FIG. 24, a method 400 of improving duty cycle of robotic system and UV emitter modules is explained, in accordance with one exemplary embodiment of the present invention. The order in which method 400 is described should not be construed as a limitation, and any number of the described method blocks can be combined in any order to implement method 400 or alternate methods. Additionally, individual blocks may be deleted from method 400 without departing from the spirit and scope of the subject matter described herein. Furthermore, method 400 may be implemented in any suitable hardware, software, firmware, or combination thereof. However, for ease of explanation, in the embodiments described below, method 400 may be implemented using the above-described robotic system 230.

As specified above, robotic system 230 may be configured to receive instructions or signal from one of first UV emitter module 210a and second UV emitter module 210b. Alternatively, robotic system 230 may be configured to receive instructions from user of user device 280. Alternatively, robotic system 230 may be pre-configured to maneuver to one of first UV emitter module 210a and second UV emitter module 210b and take it to charging dock 304 and then maneuver to pre-defined area at predefined time intervals. As such, robotic system 230 may receive instructions or signal from UV emitter e.g., first UV emitter module 210a to transport first UV emitter module 210a to charging dock 304, as shown at step 402.

Alternatively, robotic system 230 may receive instructions from user device to UV emitter e.g., first UV emitter module 210a to transport first UV emitter module 210a to charging dock 304, as shown at step 404.

After receiving the instructions (step 402 or step 404), robotic system 230 may employ first processor 237 to employ motor 245. Further, robotic system 230 may employ second sensor 241 and third sensor 242 for detecting the presence of objects or humans and location of first UV emitter module 210a, respectively. Subsequently, robotic system 230 may maneuver to the location of first UV emitter module 210a, as shown at step 406.

At step 408, robotic system 230 may mount first UV emitter module 210a using emitter interface and transport or maneuver first UV emitter module 210a to charging dock 304.

After charging battery 228 of first UV emitter module 210a, robotic system 230 may transport or maneuver first UV emitter module 210a to a predefined area or location for disinfecting using UV light source 218, as shown at step 410. In accordance with one embodiment of the present invention, when battery 228 of first UV emitter module 210a is getting charged, battery 246 may also get charged through emitter interface 236 of first UV emitter module 210a. After charging battery 228, when robotic system 230 picks up first UV emitter module 210a to take it to predefined area, battery 246 of robotic system 230 may get charged through emitter interface 236 of first UV emitter module 210a. This ensures that battery 246 of robotic system 230 gets continuously charged or recharged from connected first UV emitter module 210a.

Based on the above, it is evident that sterilization system including separate Ultraviolet (UV) emitter modules and robotic system can be used to have a 100% duty cycle for robotic system and UV emitter modules. As a result, one robotic system and two UV emitter modules may be used for near 24-hour operation without interruption thereby providing substantial savings in cost to facilities.

As robotic system and UV emitter modules are installed with sensors for detecting presence of users, they can be operated only when they detect the humans are not present in the closed environment thereby ensuring safety of users and also disinfecting the closed environment.

The sterilization system may be used in hospitals, hotels, food preparation facilities, industrial complexes, shopping malls and any other closed environment.

Although the above disclosure is generally described in which the sterilization system for improving duty cycle of robotic system and Ultraviolet (UV) emitter modules disinfecting closed environment is implemented as a single robotic system and two UV emitter modules, it should be understood that the disclosed sterilization system may be scaled up such that multiple robotic systems can be used in a single facility and multitude of UV emitter modules can be operated to improve sterilization of closed environment and also improve duty cycle of multiple robotic systems and multitude of UV emitter modules.

The present invention has been described in particular detail with respect to various possible embodiments, and those of skill in the art will appreciate that the invention may be practiced in other embodiments. First, the particular naming of the components, capitalization of terms, the attributes, data structures, or any other programming or structural aspect is not mandatory or significant, and the mechanisms that implement the invention or its features may have different names, formats, or protocols. Further, the system may be implemented via a combination of hardware and software, as described, or entirely in hardware elements. In addition, the particular division of functionality between the various system components described herein is merely exemplary, and not mandatory; functions performed by a single system component may instead be performed by multiple components, and functions performed by multiple components may instead performed by a single component.

Some portions of above description present the features of the present invention in terms of algorithms and symbolic representations of operations on information. These algorithmic descriptions and representations are the means used by those skilled in the data processing arts to most effectively convey the substance of their work to others skilled in the art. These operations, while described functionally or logically, should be understood as being implemented by computer programs.

Further, certain aspects of the present invention include process steps and instructions described herein in the form of an algorithm. It should be noted that the process steps and instructions of the present invention could be embodied in software, firmware or hardware, and when embodied in software, could be downloaded to reside on and be operated from different platforms used by real time network operating systems.

The algorithms and operations presented herein are not inherently related to any particular computer or other apparatus. Various general-purpose systems may also be used with programs in accordance with the teachings herein, or it may prove convenient to construct more specialized apparatus to perform the required method steps. The required structure for a variety of these systems will be apparent to those of skill in the, along with equivalent variations. In addition, the present invention is not described with reference to any particular programming language. It is appreciated that a variety of programming languages may be used to implement the teachings of the present invention as described herein, and any references to specific languages are provided for disclosure of enablement and best mode of the present invention.

The foregoing description of the preferred embodiments is provided to enable persons skilled in the art to make and use the present invention. Various modifications to these embodiments will be readily apparent to the persons skilled in the art. The scope of the present invention is limited only by the appended claims, and their legal equivalents.

What is claimed is:

1. A method of improving duty cycle of Ultraviolet (UV) emitter modules for disinfecting closed environment, method comprising:
   receiving, by a processor, signal corresponding to discharge of battery from one of plurality of UV emitter modules, wherein each of said plurality of UV emitter modules comprises a Ultraviolet (UV) light source for disinfecting closed environment;
   detecting, by said processor, location of a UV emitter module amongst said plurality of UV emitters;
   maneuvering, by said processor, a robotic system to location of said UV emitter module;
   mounting, by said processor, said UV emitter module to said robotic system for maneuvering said UV emitter module to charging dock for charging a battery of said UV emitter module; and
   upon charging, maneuvering, by said processor, said UV emitter module to a pre-defined area for disinfecting pre-defined area of a closed environment, such that charging respective battery of each of said plurality of UV emitter modules upon being discharged continuously improves duty cycle of plurality of UV emitter modules for disinfecting closed environment.

2. The method of claim 1, further comprises: charging the battery of said robotic system through an emitter interface provided at said robotic system when said battery of said UV emitter module gets charged or when said UV emitter module mounted to said robotic system comprises said battery that is fully charged for improving duty cycle of said plurality of UV emitter modules and said robotic system.

3. The method of claim 1, further comprises receiving, by said processor, a signal corresponding to discharge of said battery of said UV emitter module of said plurality of UV emitter modules from a user device.

4. The method of claim 1, wherein maneuvering further comprises:
   detecting, by said processor, presence of humans in the closed environment or along route while maneuvering.

5. The method of claim 3, further comprises: terminating maneuvering of said robotic system upon detecting presence of the humans in the closed environment or along route while maneuvering.

6. A robotic system in conjunction with Ultraviolet (UV) emitter modules for improving duty cycle of UV emitter modules for disinfecting closed environment, said robotic system comprising:
   a processor; and
   a memory coupled to said processor, wherein said processor is configured to execute program instructions stored in said memory, to:
      receive signal corresponding to discharge of a battery from one of plurality of UV emitter modules, wherein each of said plurality of UV emitter modules comprises a Ultraviolet (UV) light source for disinfecting closed environment;
      detect location of a UV emitter amongst said plurality of UV emitter modules;
      maneuver to the location of said UV emitter module;
      mount said UV emitter to maneuver said UV emitter module to a charging dock for charging a battery of said UV emitter module; and
      upon charging, maneuver said UV emitter module to a pre-defined area for disinfecting pre-defined area of a closed environment, such that charging respective battery of each of said plurality of UV emitter modules upon being discharged continuously improves duty cycle of said plurality of UV emitter modules for disinfecting closed environment.

7. The robotic system of claim 6, further comprises an emitter interface for mounting said UV emitter modules.

8. The robotic system of claim 7, wherein said emitter interface is used for charging the battery of said robotic system when the battery of said UV emitter module gets charged or when said UV emitter module mounted to said robotic system comprises the battery that is fully charged for improving duty cycle of said plurality of UV emitter modules and said robotic system.

9. The robotic system of claim 6, further comprises a user device communicatively connected to said robotic system, wherein said user device is configured to provide a signal corresponding to discharge of the battery of said UV emitter module to said robotic system.

10. The robotic system of claim 6, further comprises sensors configured to detect presence of humans in the closed environment or along route of said robotic system while maneuvering.

11. The robotic system of claim 8, wherein said processor is further configured to terminate maneuvering of said robotic system upon detecting presence of humans in the closed environment or along route while maneuvering.

12. A sterilization system for improving duty cycle of Ultraviolet (UV) emitter modules for disinfecting closed environment, said sterilization system comprising:
  a robotic system; and
  a first UV emitter module and a second UV emitter module, wherein each of said first UV emitter module and said second UV emitter module comprises a battery, and wherein each of said first UV emitter module and said second UV emitter module comprises a Ultraviolet (UV) light source for disinfecting a closed environment,
  wherein said robotic system is configured to:
    receive a signal corresponding to discharge of the battery from said first UV emitter module;
    detect location of said first UV emitter module;
    maneuver to location of said first UV emitter module;
    mount said first UV emitter module to maneuver said first UV emitter module to a charging dock for charging the battery of said first UV emitter module; and
    upon charging, maneuver said first UV emitter module to a pre-defined area; and
  wherein said robotic system is configured to:
    receive a signal corresponding to discharge of the battery from said second UV emitter module;
    detect location of said second UV emitter module;
    maneuver to location of second UV emitter module;
    mount said second UV emitter module to maneuver said second UV emitter module to the charging dock for charging the battery of said second UV emitter module; and
    upon charging, maneuver said second UV emitter module to a pre-defined area,
  wherein said robotic system ensures one of said first UV emitter module and said second UV emitter module is used for disinfecting the closed environment while other is charged thereby improving duty cycle of said first UV emitter module and said second UV emitter module for disinfecting the closed environment.

13. The sterilization system of claim 12, wherein said robotic system comprises an emitter interface for mounting said first UV emitter module and said second UV emitter module.

14. The sterilization system of claim 13, wherein said emitter interface is used for charging the battery of said robotic system when the battery of said first UV emitter module or said second UV emitter module get charged or when said first UV emitter module or said second UV emitter module mounts to said robotic system comprises the battery that is fully charged for improving duty cycle of said first UV emitter module and said second UV emitter module, and said robotic system.

15. The sterilization system of claim 12, further comprises a user device configured to provide a signal corresponding to discharge of the battery of said first UV emitter module and said second UV emitter module.

16. The sterilization system of claim 12, wherein said robotic system comprises sensors configured to detect presence of humans in the closed environment or along route while maneuvering.

17. The sterilization system of claim 12, wherein said robotic system is configured to terminate maneuvering upon detecting presence of humans in the closed environment or along route while maneuvering.

18. The sterilization system of claim 12, wherein each of said first UV emitter module and said second UV emitter module comprises a UV sensor configured to measure intensity of UV radiation produced by said UV light source of respective said first UV emitter module and said second UV emitter module.

19. The sterilization system of claim 12, wherein each of said first UV emitter module and said second UV emitter module comprises a sensor configured to detect presence of humans to operate or terminate said UV light source for disinfecting the closed environment.

20. The sterilization system of claim 12, wherein each of said first UV emitter module and said second UV emitter module comprises size different from other to provide varied UV radiation for disinfecting the pre-defined area in the closed environment.

* * * * *